(12) United States Patent
Wright

(10) Patent No.: US 10,787,681 B2
(45) Date of Patent: Sep. 29, 2020

(54) HUMANIZED VIRAL VECTORS AND METHODS OF USE THEREOF

(71) Applicant: The Children's Hospital of Philadelphia, Philadelphia, PA (US)

(72) Inventor: John Fraser Wright, Princeton, NJ (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 15/411,489

(22) Filed: Jan. 20, 2017

(65) Prior Publication Data

US 2017/0128594 A1 May 11, 2017

Related U.S. Application Data

(63) Continuation of application No. 12/581,684, filed on Oct. 19, 2009, now abandoned, which is a continuation-in-part of application No. PCT/US2008/060654, filed on Apr. 17, 2008.

(60) Provisional application No. 60/912,193, filed on Apr. 17, 2007.

(51) Int. Cl.
| | | |
|---|---|---|
| *C12N 15/85* | (2006.01) | |
| *C12N 15/86* | (2006.01) | |
| *C07K 14/765* | (2006.01) | |
| *A61K 48/00* | (2006.01) | |
| *C12N 15/864* | (2006.01) | |
| *A61K 38/48* | (2006.01) | |
| *A61K 47/12* | (2006.01) | |
| *A61K 47/42* | (2017.01) | |
| *C12N 7/00* | (2006.01) | |
| *C12N 9/64* | (2006.01) | |

(52) U.S. Cl.
CPC .......... *C12N 15/86* (2013.01); *A61K 38/4846* (2013.01); *A61K 47/12* (2013.01); *A61K 47/42* (2013.01); *A61K 48/00* (2013.01); *C07K 14/765* (2013.01); *C12N 7/00* (2013.01); *C12N 9/644* (2013.01); *C12N 15/8645* (2013.01); *C12Y 304/21022* (2013.01); *C12N 2750/14143* (2013.01); *C12N 2750/14145* (2013.01); *C12N 2810/85* (2013.01)

(58) Field of Classification Search
CPC ............................ C12N 15/8645; A61K 48/00
See application file for complete search history.

(56) References Cited

U.S. PATENT DOCUMENTS

| | | |
|---|---|---|
| 5,789,230 A | 8/1998 | Cotten |
| 6,846,809 B2 | 1/2005 | Cristiano et al. |
| 2002/0151060 A1 | 10/2002 | Cristiano et al. |
| 2002/0160393 A1 | 10/2002 | Symonds et al. |
| 2004/0002159 A1 | 1/2004 | Xiao et al. |
| 2004/0029280 A1 | 2/2004 | Sosnowski et al. |
| 2004/0110678 A1 | 6/2004 | Silligardi et al. |

OTHER PUBLICATIONS

Chillon et al., Adenovirus Complexed With Polyethylene Glycol and Cationic Lipid is Shielded From Neutralizing Antibodies in vitro, Gene Ther., 1998, 5:995-1002.
Cross-link Wikipedia Printout (http://en.wikipedia.org/wiki/Cross-link. pp. 1-6, printed Apr. 23, 2015).
Crosslink definition—Google search printout (pp. 1-2, printed Apr. 23, 2015).
Hedley et al., Targeted and Shielded Adenovectors for Cancer Therapy, Cancer Immunol. Immunother., 2006, 55:1412-1419.
Koeberl et al., Persistent Expression of Human Clotting Factor IX from Mouse Liver After Intravenous Injection of Adeno-Associated Virus Vectors, Proc. Natl. Acad. Sci. USA, 1997, 94(4):1426-31.
Lee et al., Chapter 20:Albumin Modification in Scaffolding in Tissue Engineering. Ma and Elisseeff (eds.) CRC PressTaylor and Francis Group: Boca Raton, 2006. See pp. 283, 284, 289, and 290.
Ponnazhagan et al., Conjugate-Based Targeting of Recombinant Adeno-Associated Virus Type 2 Vectors by Using Avidin-Linked Ligands, Journal of Virology, 2002, 76(24):12900-12907.
Ponnazhagan, Selvarangan, et al. "Conjugate-based targeting of recombinant adeno-associated virus type 2 vectors by using avidin-linked ligands." Journal of virology 76.24 (2002): 12900-12907.†

† cited by third party

*Primary Examiner* — Marcia S Noble
(74) *Attorney, Agent, or Firm* — Pillsbury Winthrop Shaw Pittman LLP; Robert M. Bedgood

(57) ABSTRACT

The present invention provides humanized viral vectors and methods of use thereof for delivery of transgenes or therapeutic nucleic acids to human subjects. Humanized viral vectors are modified from known viral vectors such as those based on AAV by coating their surface with a human protein such as human serum albumin and optionally a lipid coating or formulation, so that the foreign or non-human nature of the vector is masked. The coating is performed in a manner that reduces or prevents binding of antibodies to the vector surface, thereby reducing or preventing antibody-mediated clearance of vector, but still allowing the vector to transduce target cells and achieve therapeutic gene transfer. Such humanized vectors therefore evade pre-existing immune surveillance, reduce immune responses, and achieve therapeutic gene transfer in the presence of pre-existing antibodies to the viral vector.

12 Claims, 18 Drawing Sheets

HUMANIZED VIRAL VECTORS AND METHODS OF USE THEREOF

RELATED APPLICATIONS

This application is a continuation application of application Ser. No. 12/581,684, filed Oct. 19, 2009, which is a continuation in part of international application no. PCT/US2008/060654, filed Apr. 17, 2008, which claims the benefit of priority to provisional application No. 60/912,193, filed Apr. 17, 2007, all of which applications are expressly incorporated herein by reference in their entirety.

FIELD OF THE INVENTION

This application relates to the fields of gene therapy and molecular biology. More specifically, this invention provides humanized viral vectors which evade immune surveillance, thereby providing for more efficient and predictable expression of therapeutic polynucleotides and polypeptides, greater duration of expression, and the capacity for re-administration in the presence of existing anti-vector immunity. Preferably, the viral vector is an adeno-associated virus vector.

BACKGROUND OF THE INVENTION

Several publications and patent documents are cited throughout the specification in order to describe the state of the art to which this invention pertains. Each of these citations is incorporated herein by reference as though set forth in full.

A variety of gene delivery vectors have been developed that can achieve delivery of therapeutic genes to mammalian cells in vitro and in vivo. Some of these are viral vectors which are based on common viruses, for example, adeno-associated virus, Type 2 (AAV2). Structurally, AAV2 is a relatively simple virus, is ubiquitous in the human population and is not known to cause disease. Genetically modified (recombinant) AAV2 has been studied extensively as a gene delivery vector with potential to effectively treat many serious and chronic diseases in humans. More recently additional serotypes of AAV have been described that further expand the promise of these vectors for therapeutic gene transfer. Studies performed using a number of different animal models have demonstrated that AAV vectors can mediate transfer and expression of genes encoding therapeutic proteins such as blood coagulation factors VIII (Scallan, et al.) and IX (Herzog et al. 1999), Synder et al., (1999) and monoclonal antibodies (Lewis et al. 2002) and several other proteins of potential therapeutic clinical benefit. Human clinical trials in which AAV2 vectors expressing human coagulation factor IX were administered confirmed their ability to deliver therapeutic levels of human coagulation factor IX (High et al. 2003; Manno et al. 2006). However, pre-existing immunity to AAV2, and adaptive immune responses to the non-human components (e.g., viral capsid proteins) of AAV-based gene transfer vectors remains a barrier to achieving consistent and efficient gene transfer and long term expression of therapeutic genes in humans.

SUMMARY OF THE INVENTION

In accordance with the present invention, a humanized viral vector containing a transgene encoding a therapeutic protein or polynucleotide of interest which evades immune surveillance is provided. In preferred embodiments the viral vector is an adeno-associated viral vector.

The present inventor has developed a viral vector gene delivery system wherein the viral vector comprises human proteins affixed to the capsid surface which are recognized as "self" proteins by the human immune system. Coating the capsid with human proteins masks the antigenic viral epitopes, precluding recognition by antibodies and thereby reducing antibody mediated clearance and immune responses. Accordingly, delivery of the transgene in the present system can occur in the presence of pre-existing antibodies, and is predicted to occur with higher efficiency and consistency as the viral vector is not cleared by antibody mediated mechanisms. Additionally, the humanized viral vectors may be administered multiple times because of their ability to evade recognition by antibodies.

In preferred embodiments the human protein is human serum albumin, however a variety of human proteins may be employed for this purpose. In alternative embodiment, the human protein is attached to or embedded within a lipid membrane that surrounds the viral vector capsid particle or a plurality of particles. In yet another embodiment, a targeting moiety other than a human protein, such as a carbohydrate or lipid, may substitute for a human protein.

In alternative embodiment, the human protein is a complex of a protein and a ligand. Preferably, the complex comprises human serum albumin (the protein) and heparin (the ligand).

In another aspect of the invention, pharmaceutical compositions comprising the humanized viral vectors described herein in a pharmaceutically acceptable carrier are provided. Methods for delivering a transgene encoding a desirable heterologous protein or peptide of interest or therapeutic nucleic acid to a cell comprising administration of an effective amount of the pharmaceutical composition described herein to a patient in need thereof are also encompassed by the present invention. Finally, kits comprising reagents necessary to perform the methods described above are also within the scope of the invention.

BRIEF DESCRIPTION OF THE DRAWINGS

FIG. 8B shows the A20 association curves, provided at concentration ranging from approximately 0.067 nM to 6.7 nM, to immobilized AAV2LacZ. FIG. 8B shows the A20 association curves using the same A20 concentration range and timeframe, to AAV2LacZ-HSA/$_{RHi}$. These data support the presence of fewer A20 binding sites on the HSA-conjugated vectors compared to unmodified AAV2LacZ, and support that the binding affinity of A20 binding to the HSA-conjugated vectors is lower than the binding affinity of A20 binding to unmodified AAV2LacZ.

DETAILED DESCRIPTION OF THE INVENTION

Figure 1:
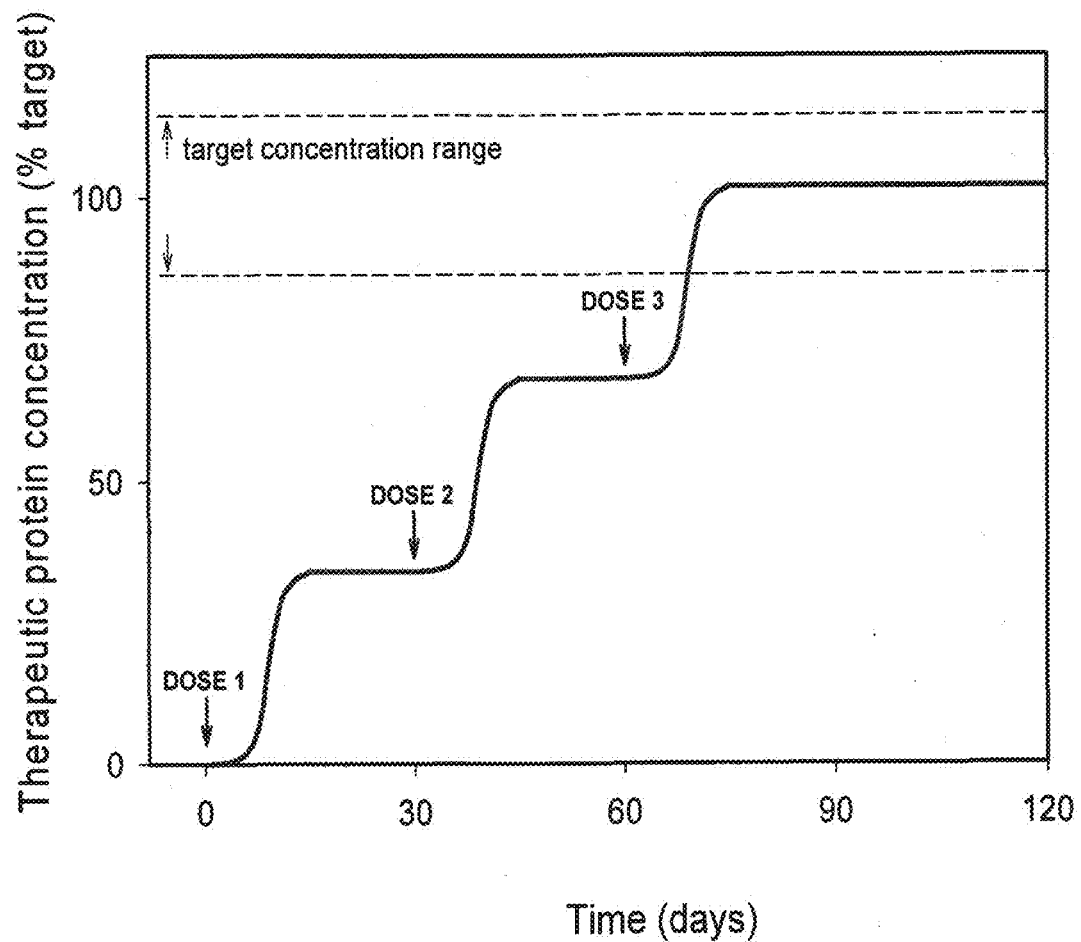
FIG. 1. A graph illustrating that humanized AAV vectors should enable gradual increases in therapeutic product concentration by enabling incremental dosing in a human subject that may have pre-existing antibodies to AAV, and/or who will develop antibodies to AAV following administration of AAV vectors. If they are present, pre-existing antibodies to AAV are known to block efficient transduction of target tissues for several important routes of administration. Even if pre-existing antibodies are not present, a single administration of an AAV vector will cause the production of antibodies that will block transduction associated with subsequent administration, significantly limiting the usefulness of viral vector based gene transfer for many important routes of administration. In contrast, the humanized vectors described herein should provide more efficient transduction in the presence of antibodies specific to viral proteins, whether the antibodies are pre-existing or whether they are caused (or increased) by administration of the therapeutic agent. Humanized viral vectors should also facilitate sequential dosing using an appropriate humanized viral vector in each individual who may benefit from therapeutic gene transfer. Sequential dosing is predicted to enhance safety of treatment because treatment can be initiated with a small dose, assessed for a period to monitor for adverse effects before proceeding with additional doses to gradually reach the target concentration of the therapeutic gene product.
Figure 2:
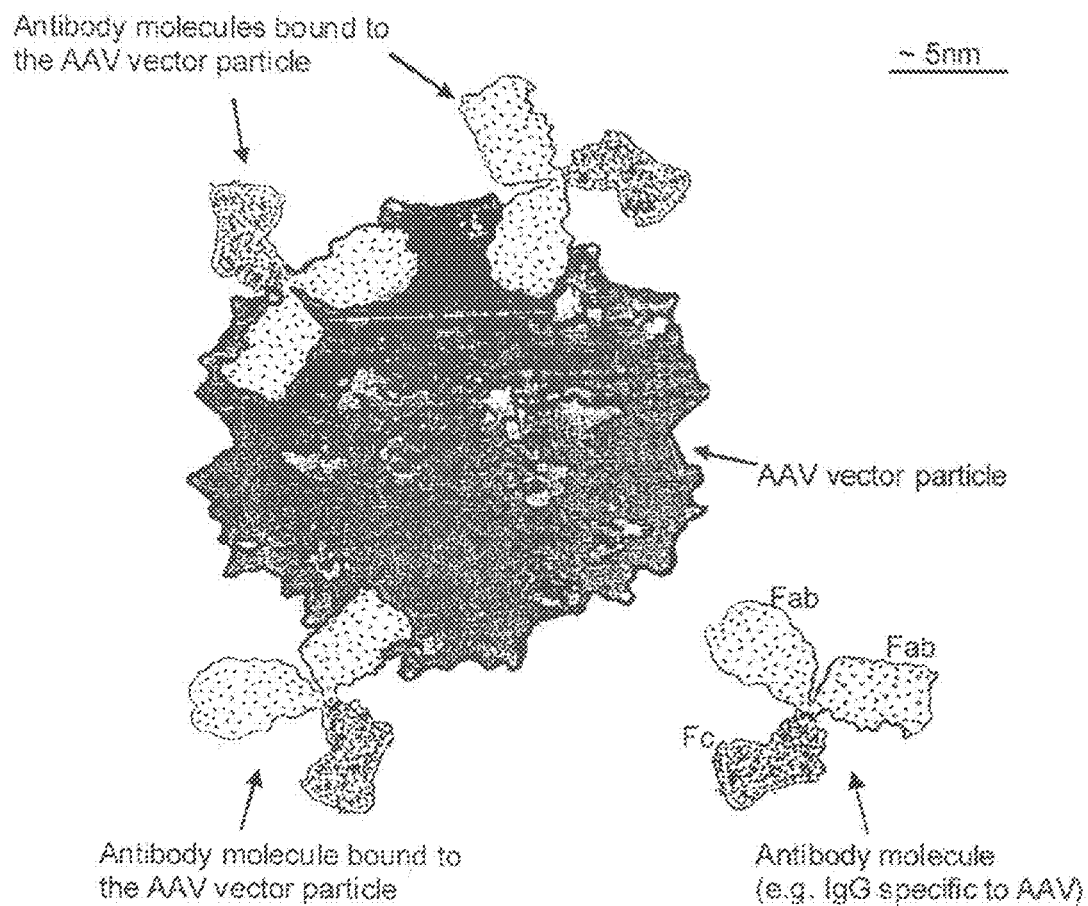
FIG. 2. Representation of one AAV particle and four Antibody molecules, showing three Antibody molecules bound to the surface of the AAV particle. Pre-existing antibodies (e.g Immunoglobulin G (IgG)) to AAV2 may be present in the blood and other body fluids of most humans, and are predicted to bind to the surface of AAV2 vectors. The figure shows one AAV2 particle and four antibody molecules drawn approximately to scale. The antigen binding regions on one or both of the Fab portions (shown by lower density shading) of the antibody molecules may bind to specific epitopes on the surface of the AAV vector particle. Once bound (three examples of vector-bound antibody are shown) the vector particle is opsonized, i.e. the vector particle is 'flagged' or 'marked' for elimination by the immune system. For example, the opsonized particle may bind to antigen presenting cells (such as Kupffer cells in the liver sinusoids) that express Fc Receptors (FcR) that recognize the Fc regions of the antibody molecules.
Figure 3:
FIG. 3. Pathways and likely fate of blood-borne, antibody-opsonized AAV vector particles in human liver. AAV particles that have been opsonized by antibodies are likely to interact with FcR's expressed on Kupffer cells that are present in the lining of liver capillaries. The AAV particles have to pass the Kupffer cells to reach the hepatocytes, which are the target cells for gene transfer. Kupffer cells play a key role in binding opsonized non-self (foreign) antigens, which results in an immune response directed specifically to the non-self antigen. Once bound to the Kupffer cells, the vector is likely to be internalized by the Kupffer cell, and subjected to processing and presentation resulting in the amplification of an immune response directed against the vector. Thus, few if any few AAV particles avoid being bound to Kupffer cell FcR's reach the intended target AAV receptors on hepatocytes. In this figure, only one AAV particle has successfully reached the intended target heptocyte.
Figure 4:
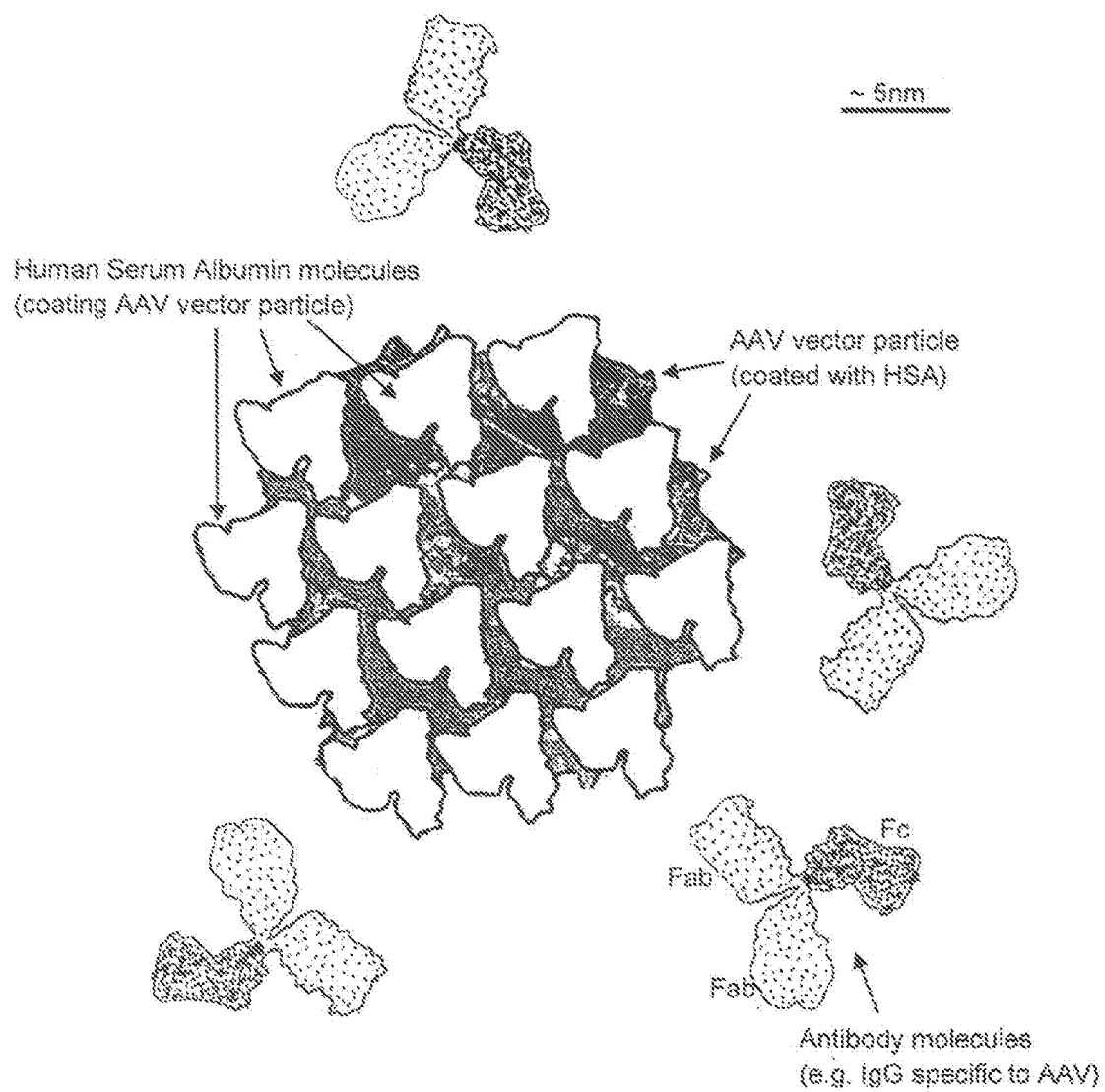
FIG. 4. A schematic representation of one AAV particle that has been coated with human serum albumin (an example of a humanized AAV particle), and four Antibody molecules that are blocked from binding to the surface of the AAV particle is shown. Pre-existing antibodies to AAV do not bind to the surface of 'humanized' AAV vectors (huAAV vectors). This figure shows one AAV2 particle coated with many molecules of human serum albumin (HSA) in a manner such that antibodies to the AAV vector are not able to bind to the surface of the vector. Because HSA is a human (self) protein, antibodies to HSA are not expected to be present, and are unlikely to be generated, even after re-administration of the huAAV vectors.
Figure 5:
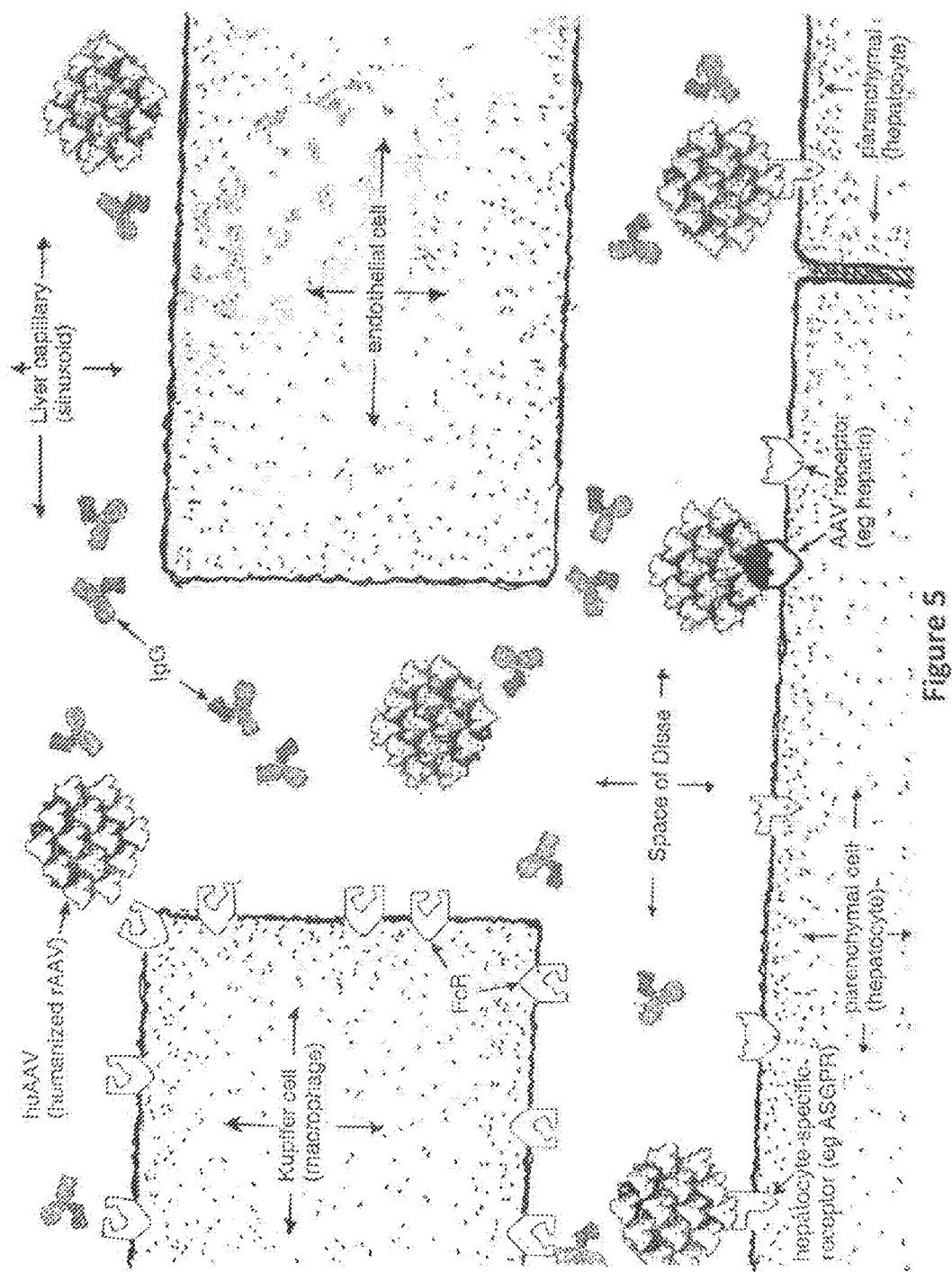
FIG. 5. Pathways and likely fate of blood-borne humanized AAV particles in human liver. Humanized AAV particles are not opsonized by antibodies, not recognized by Kupffer cell Fc Receptors, and therefore are less likely to activate an immune response to the AAV vectors. Instead the huAAV vector particles should bypass the Kupffer cells, reaching and successfully transducing the intended target hepatocytes. Appropriately designed and prepared huAAV vectors may bind and enter hepatocytes following binding to hepatocytes specific receptors. Alternatively, if the coating protein (e.g. HSA) is attached non-covalently to the vector surface, displacement of some HSA molecules by AAV receptors present at high density on the surface of hepatocytes is possible, leading to vector uptake and successful gene transfer to these cells.

In accordance with the present invention, a general strategy and specific methods for making "humanized" adeno-associated virus-based vectors (huAAV vectors) which are not recognized by antibodies to AAV are provided.

Pre-existing immunity to AAV2, and the immune response induced by the administration of AAV2 vectors are significant barriers to achieving long-term expression of therapeutic proteins. Accordingly, a strategy that effectively reduces or prevents recognition of AAV vectors by important elements of the immune system, such as vector specific antibodies, and thereby reduces or prevents activation of the human immune response following AAV vector administration should result in more efficient, consistent gene transfer and more efficacious, long term transgene expression. Such a strategy will dramatically improve the usefulness of AAV vectors.

Strategies have been previously reported that aim to overcome pre-existing immunity to AAV2 vectors. These include the use of "alternative serotypes" or subtypes of AAV (Gao et al. (2002)) to which human subjects have not previously been exposed. The use of "alternative serotypes" may overcome the problem of pre-existing antibodies for a single administration of an AAV vector. However, after this initial administration the treated individual will produce antibodies specific for the alternative AAV serotype vector that are predicted to interfere with subsequent administration of that vector. Another strategy that has been reported is the covalent attachment of the chemical compound polyethylene glycol (PEG) to the surface of AAV vector particles (Le et al. (2005)). This approach was reported to reduce binding of pre-existing AAV antibodies to the modified virus. However, "PEGylation" of AAV vectors is predicted to reduce target cell transduction efficiency, alter biodistribution following in vivo administration, and result in formation of antibodies to the modified vector following an initial administration that would interfere with their subsequent administration.

A significant problem with currently described strategies for therapeutic gene administration using viral vectors is that re-administration using the same vector construct is expected to be ineffective because generation of antibodies generated following the first administration prevents target cell transduction following subsequent administration(s) of the vector. If achievable, the ability to re-administer a given vector to achieve therapeutic gene delivery spread out over multiple administrations would be a significant advance. Such incremental gene dosing through multiple administrations of the vector would also represent an important safety feature, because it would be possible to start at a low dose and increase gene transfer stepwise to achieve a desired therapeutically effective level.

The general strategy described herein entails the attachment of normal, "self" human proteins to the surface of AAV based gene transfer vectors to coat the surface so that antibodies to AAV are blocked from binding to the vector. The attachment of human proteins to the vector may be achieved by covalent or non-covalent bonds. It may be useful to use an intermediate molecule, herein referred to as a ligand, that may be attached covalently or non-covalently to the human proteins or surface of vectors in an initial step in making the human protein coated vector particle. It is important that the size of the coating protein, and the chemistry and stoichiometry of the coating protein-vector interaction is such that the coating protein effectively coats vector particles to the degree necessary to substantially reduce or eliminate antibody binding potential, but does not cause deleterious consequences such as vector aggregation. An exemplary approach entails producing a derivative of human serum albumin (HSA) that has one molecule of heparin (or a similar molecule) per molecule of HSA attached to amino acid residue Cys34 of HSA. When mixed with recombinant AAV2, mono-heparin HSA is predicted to bind and coat the surface of AAV2 vector particles via vector surface heparin binding sites known to be present on the surface of AAV2 (Xie et al, 2002). The affinity of the known heparin binding sites on AAV2 could be modulated (increase or decreased) to optimize the affinity of the non-covalent interaction of mono-heparin HSA by changing amino acids within or proximal to the heparin binding site of AAV2 using molecular biology techniques that are well established. Alternatively, the human protein may be embedded within a lipid envelope which surrounds the AAV capsid particle. In this case, the lipid envelope, preferably a phospholipid bilayer similar to those commonly found in human blood constituents (i.e. a lipid envelope that appears as human in nature and therefore will be not activate the human immune system), will help to: 1) shield the AAV capsid surface from antibodies; and 2) provide a structure into or onto which human proteins can associate. Alternatively, other biological molecules, e.g., a carbohydrate moiety, can be used in place of the human protein. These carbohydrate moieties are optionally attached to a lipid as one of the constituents of the lipid envelope, for example commercially available phosphoethanolamine-N-lactosyl (Lactosyl PE). The lipid-enveloped versions of humanized AAV vectors described herein include all of the following components together: 1) the vector genome (a therapeutic expression cassette flanked by AAV inverted terminal repeats); 2) the AAV capsid; 3) the lipid envelope; and 4) the non immunogenic cell targeting moieties (e.g. human protein or carbohydrate), each providing a distinct and critical role. The combination of these four features together enhancing delivery of transgenes for human gene therapy applications.

Antibodies to AAV2 are often present in the blood and body fluids of humans because natural AAV2 infection is common, and such antibodies may be induced and/or elevated when recombinant AAV is administered to human subjects in the course of clinical studies and/or treatment using recombinant AAV. Such antibodies should not bind to the huAAV vectors described herein. Due to their ability to evade antibody-mediated immune clearance, the huAAV vectors described herein 1) enable consistent and efficient therapeutic gene delivery in vivo in the presence of pre-existing AAV antibodies; and 2) prevent undesired targeting of AAV vectors to human immune cells (via vector bound IgG/immune cell FcR interactions), thereby reducing activation of components of the adaptive immune response that may be responsible for preventing long term expression of therapeutic transgene in vivo.

I. Definitions

"Gene therapy" is the insertion of genes into an individual's cells and/or tissues to treat a disease, commonly hereditary diseases wherein a defective mutant allele is replaced or supplemented with a functional one.

"Adeno-associated viruses", from the parvovirus family, are small viruses with a genome of single stranded DNA. These viruses can insert genetic material at a specific site on chromosome 19 and are preferred because they are not associated with pathogenic disease in humans.

A "human protein" for use in the humanized vectors of the invention is preferably a highly conserved protein which would not be recognized as a foreign or non-self antigen by the human immune system. While human serum albumin is exemplified herein, other proteins which would be useful for this purpose include, without limitation, fibrinogen A, fibrinogen B, beta-2-microglobulin, zinc-alpha-2-glycoprotein, alpha-2-HS-glycoprotein (fetuin), serum amyloid protein A, haptoglobin, profilin, desmocollin, thymosin beta-4 and -beta-10, apolipoprotein uteroglobin, ubiquitin, gelsolin, collagen, fibrin, as well as fragments of these and other human proteins.

A "therapeutic" peptide or protein is a peptide or protein that may alleviate or reduce symptoms that result from an absence or defect in a protein in a cell or subject. Alternatively, a "therapeutic" peptide or protein is one that otherwise confers a benefit to a subject, e.g., anti-cancer effects. Therapeutic peptides and proteins include, but are not limited to, CFTR (cystic fibrosis transmembrane regulator protein), dystrophin (including the protein product of dystrophin mini-genes, see, e.g, Vincent et al., (1993) Nature Genetics 5:130), utrophin (Tinsley et al., (1996) Nature 384:349), clotting factors (Factor XIII, Factor IX, Factor X, etc.), monoclonal antibodies (Lewis et al., 2002), erythropoietin, the LDL receptor, lipoprotein lipase, ornithine transcarbamylase, β-globin, α-globin, spectrin, α-antitrypsin, adenosine deaminase, hypoxanthine guanine phosphoribosyl transferase, β-glucocerebrosidase, sphingomyelinase, lysosomal hexosaminidase, branched-chain keto acid dehydrogenase, hormones, growth factors (e.g., insulin-like growth factors 1 and 2, platelet derived growth factor, epidermal growth factor, nerve growth factor, neurotrophic factor-3 and -4, brain-derived neurotrophic factor, glial derived growth factor, transforming growth factor α and β, and the like), cytokines (e.g., α-interferon, β-interferon, interferon-γ, interleukin-2, interleukin-4, interleukin 12, granulocyte-macrophage colony stimulating factor, lymphotoxin), suicide gene products (e.g., herpes simplex virus thymidine kinase, cytosine deaminase, diphtheria toxin, cytochrome P450, deoxycytidine kinase, and tumor necrosis factor), proteins conferring resistance to a drug used in cancer therapy, tumor suppressor gene products (e.g., p53, Rb, Wt-1, NF1, VHL, APC, and the like), and any other peptide or protein that has a therapeutic effect in a subject in need thereof.

Further exemplary therapeutic peptides or proteins include those that may used in the treatment of a disease condition including, but not limited to, cystic fibrosis (and other diseases of the lung), hemophilia A, hemophilia B, thalassemia, anemia and other blood disorders, AIDS, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Gaucher's disease, Hurler's disease, adenosine deaminase deficiency, glycogen storage diseases and other metabolic defects, retinal degenerative diseases (and other diseases of the eye), and diseases of solid organs (e.g., brain, liver, kidney, heart).

A "therapeutic nucleic acid molecule" refers to small nucleic acid molecules which are capable of modulating expression levels of a target mRNA, (e.g., siRNA, shRNA, miRNA, antisense oligonucleotides etc.). Preferably such molecules are able to inhibit expression of a target gene involved in mediation of a disease process, thereby preventing or alleviating symptoms of a disease. A "siRNA" refers to a molecule involved in the RNA interference process for a sequence-specific post-transcriptional gene silencing or gene knockdown. siRNAs have homology with the sequence of the cognate mRNA of the targeted gene. Small interfering RNAs (siRNAs) can be synthesized in vitro or generated by ribonuclease III cleavage from longer dsRNA and are the mediators of sequence-specific mRNA degradation. Preferably, the siRNA or therapeutic nucleic acids of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting the mRNA of a target gene may be between 15-35 nucleotides in length, and more typically about 21 nucleotides in length. Such therapeutic nucleic acid molecules can be readily incorporated into the humanized viral vectors disclosed herein using conventional methods known to the person skilled in the art of molecular biology.

Lipids are organic biomolecules. There are several classes of lipids but all derive their distinctive properties from the hydrocarbon nature of a major portion of their structure. Lipid formulations as described herein refer to simple and complex lipids, including acylglycerols, phosphoglycerides (phospholipids) such as phosphatidyl-choline, phosphatidyle serine, phosphatidyle-ethanolamine, sphingolipids, fatty acids, triacylglycerols (triglycerides), alkyl ether acylglycerols, glycosylacylglycerols, phosphoglycerides, (glycerol phosphatides), sphingolipids, waxes, terpenes, steroids, and prostaglandins. Lipids as described herein also include anionic lipids, neutral lipids, cationic lipids, fatty acid modified lipids, headgroup modified lipids such as functionalized lipids, adhesive lipids, and glycosylated lipids (for example lactosyl phosphatidyl ethanolamine (lactosyl PE)). Lipids as described herein also include poloxamers. A well known feature of some lipids, such as certain phosphoglycerides (phospholipids) preferred for the formation of lipid enveloped versions of humanized AAV vectors, is their ability to form liposomes, which are complete closed, vesicular bilayer structures that can be formed by exposing phosphoglyceride aqueous solutions to certain physicochemical conditions such as sonication or agitation by vortexing.

Carbohydrates are polyhydroxy aldehydes or ketones and their derivatives. Many have the empirical formula $(CH_2O)n$. Carbohydrates include monosaccharides, also called simple sugars, consisting of a single polyhydroxy aldehyde or ketone unit. Carbohydrates include oligosaccharides containing from two to ten or more monosaccharide units joined in glycosidic linkage. Carbohydrates included polysaccharides containing many monosaccharide units joined in linear or branched chains. Carbohydrates as described herein also include glycosides, N-glycosylamines, O-acyl derivatives, O-methyl derivatives, osazones, sugar alcohols, sugar acids, sugar phosphates, deoxy sugars, amino sugars, muramic acid and neuraminic acid. Carbohydrates as described herein also include disaccharides, trisaccharides, polysaccharides (glycans), storage polysaccharides such as starch, dextrans, fructans, mannans, xylans, and arabinans. Carbohydrates as described herein also include structural polysaccharides, acid mucopolysaccharides, and glycoproteins.

The term "promoters" or "promoter" as used herein can refer to a DNA sequence that is located adjacent to a DNA sequence that encodes a recombinant product. A promoter is preferably linked operatively to an adjacent DNA sequence. A promoter typically increases an amount of recombinant product expressed from a DNA sequence as compared to an amount of the expressed recombinant product when no promoter exists. A promoter from one organism can be utilized to enhance recombinant product expression from a DNA sequence that originates from another organism. For example, a vertebrate promoter may be used for the expression of jellyfish GFP in vertebrates. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art.

In one embodiment, high-level constitutive expression will be desired. Examples of such promoters include, without limitation, the retroviral Rous sarcoma virus (RSV) LTR promoter/enhancer, the cytomegalovirus (CMV) immediate early promoter/enhancer (see, e.g., Boshart et al, Cell, 41:521-530 (1985)), the SV40 promoter, the dihydrofolate reductase promoter, the cytoplasmic β-actin promoter and the phosphoglycerol kinase (PGK) promoter.

In another embodiment, inducible promoters may be desired. Inducible promoters are those which are regulated by exogenously supplied compounds, either in cis or in trans, including without limitation, the zinc-inducible sheep metallothionine (MT) promoter; the dexamethasone (Dex)-inducible mouse mammary tumor virus (MMTV) promoter; the T7 polymerase promoter system (WO 98/10088); the tetracycline-repressible system (Gossen et al, Proc. Natl. Acad. Sci. USA, 89:5547-5551 (1992)); the tetracycline-inducible system (Gossen et al., Science, 268:1766-1769 (1995); see also Harvey et al., Curr. Opin. Chem. Biol., 2:512-518 (1998)); the RU486-inducible system (Wang et al., Nat. Biotech., 15:239-243 (1997) and Wang et al., Gene Ther., 4:432-441 (1997)]; and the rapamycin-inducible system (Magari et al., J. Clin. Invest., 100:2865-2872 (1997); Rivera et al., Nat. Medicine. 2:1028-1032 (1996)). Other types of inducible promoters which may be useful in this context are those which are regulated by a specific physiological state, e.g., temperature, acute phase, or in replicating cells only.

In another embodiment, the native promoter for the transgene or nucleic acid sequence of interest will be used. The native promoter may be preferred when it is desired that expression of the transgene or the nucleic acid sequence should mimic the native expression. The native promoter may be used when expression of the transgene or other nucleic acid sequence must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In one embodiment, the recombinant viral genome comprises a transgene operably linked to a tissue-specific promoter. For instance, if expression in skeletal muscle is desired, a promoter active in muscle may be used. These include the promoters from genes encoding skeletal α-actin, myosin light chain 2A, dystrophin, muscle creatine kinase, as well as synthetic muscle promoters with activities higher than naturally-occurring promoters. See Li et al., Nat. Biotech., 17:241-245 (1999). Examples of promoters that are tissue-specific are known for liver albumin, Miyatake et al. J. Virol., 71:5124-32 (1997); hepatitis B virus core promoter, Sandig et al., Gene Ther. 3:1002-9 (1996); alpha-fetoprotein (AFP), Arbuthnot et al., Hum. Gene Ther., 7:1503-14 (1996)], bone (osteocalcin, Stein et al., Mol. Biol. Rep., 24:185-96 (1997); bone sialoprotein, Chen et al., J. Bone Miner. Res. 11:654-64 (1996)), lymphocytes (CD2, Hansal et al., J. Immunol., 161:1063-8 (1998); immunoglobulin heavy chain; T cell receptor a chain), neuronal (neuron-specific enolase (NSE) promoter, Andersen et al. Cell. Mol. Neurobiol., 13:503-15 (1993); neurofilament light-chain gene, Piccioli et al., Proc. Natl. Acad. Sci. USA, 88:5611-5 (1991); the neuron-specific vgf gene, Piccioli et al., Neuron, 15:373-84 (1995)]; among others.

The term "enhancers" or "enhancer" as used herein can refer to a DNA sequence that is located adjacent to the DNA sequence that encodes a recombinant product. Enhancer elements are typically located upstream of a promoter element or can be located downstream of or within a coding DNA sequence (e.g., a DNA sequence transcribed or translated into a recombinant product or products). Hence, an enhancer element can be located 100 base pairs, 200 base pairs, or 300 or more base pairs upstream or downstream of a DNA sequence that encodes recombinant product. Enhancer elements can increase an amount of recombinant product expressed from a DNA sequence above increased expression afforded by a promoter element. Multiple enhancer elements are readily available to persons of ordinary skill in the art.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, infection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The phrase "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to a DNA oligonucleotide, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "isolated" may refer to a compound or complex that has been sufficiently separated from other compounds with which it would naturally be associated. "Isolated" is not meant to exclude artificial or synthetic mixtures with other compounds or materials, or the presence of impurities that do not interfere with fundamental activity or ensuing assays, and that may be present, for example, due to incomplete purification, or the addition of stabilizers.

The term "immune response" is meant to refer to any response to an antigen or antigenic determinant by the immune system of a vertebrate subject. Exemplary immune responses include humoral immune responses (e.g. production of antigen-specific antibodies) and cell-mediated immune responses (e.g. lymphocyte proliferation), as defined herein below.

II. Methods of Using and Methods of Administration of the Humanized Adenoassociated Viral Vectors of the Invention The methods of the present invention provide a means for delivering heterologous nucleic acid sequences into a broad range of host cells, including both dividing and non-dividing cells. The vectors and other reagents, methods and pharmaceutical formulations of the present invention are additionally useful in a method of administering a protein, peptide or therapeutic nucleic acid to a subject in need thereof, as a method of treatment. In this manner, the protein, peptide or therapeutic nucleic acid may thus be produced in vivo in the subject. The subject may be in need of the protein or peptide because the subject has a deficiency of the protein or peptide, or because the production of the protein or peptide in the subject may impart some therapeutic effect, as a method of treatment or otherwise, and as explained further below. Alternatively, it may be desirable to down regulate a target gene involved in a disease process, e.g., for the treatment of cancer or atherosclerosis for example to achieve a therapeutic effect.

In general, the present invention may be employed to deliver any foreign nucleic acid with a biological effect to treat or ameliorate the symptoms associated with any disorder related to gene expression. Illustrative disease states include, but are not limited to: cystic fibrosis (and other diseases of the lung), hemophilia A, hemophilia B, thalassemia, anemia and other blood coagulation disorders, AIDs, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Gaucher's disease, Hurler's disease, adenosine deaminase deficiency, glycogen storage diseases and other metabolic defects, retinal degenerative diseases (and other diseases of the eye), diseases of solid organs (e.g., brain, liver, kidney, heart), and the like.

In addition, the present invention may be employed to deliver nucleic acids encoding monoclonal antibodies or fragments thereof that are known to provide beneficial biological effects to treat or ameliorate the symptoms associated with cancers, infectious diseases, and autoimmune diseases such as rheumatoid arthritis.

Gene transfer has substantial potential use in understanding and providing therapy for disease states. There are a number of inherited diseases in which defective genes are known and have been cloned. In some cases, the function of these cloned genes is known. In general, the above disease states fall into two classes: deficiency states, usually of enzymes, which are generally inherited in a recessive manner, and unbalanced states, at least sometimes involving regulatory or structural proteins, which are inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus the methods of the present invention permit the treatment of genetic diseases. As used herein, a disease state is treated by partially or wholly remedying the deficiency or imbalance that causes the disease or makes it more severe. The use of site-specific integration of nucleic sequences to cause mutations or to correct defects is also possible.

Finally, the instant invention finds further use in diagnostic and screening methods, whereby a gene of interest is transiently or stably expressed in a cell culture system, or alternatively, a transgenic animal model.

III. Subjects, Pharmaceutical Formulations, Vaccines, and Modes of Administration The present invention finds use in both veterinary and medical applications. Suitable subjects include both avians and mammals, with mammals being preferred. The term "avian" as used herein includes, but is not limited to, chickens, ducks, geese, quail, turkeys and pheasants. The term "mammal" as used herein includes, but is not limited to, humans, bovines, ovines, caprines, equines, felines, canines, lagomorphs, etc. Human subjects are the most preferred. Human subjects include fetal, neonatal, infant, juvenile and adult subjects.

In particular embodiments, the present invention provides a pharmaceutical composition comprising a virus particle of the invention in a pharmaceutically-acceptable carrier or other medicinal agents, pharmaceutical agents, carriers, adjuvants, diluents, etc. For injection, the carrier will typically be a liquid. For other methods of administration, the carrier may be either solid or liquid, such as sterile, pyrogen-free water or sterile pyrogen-free phosphate-buffered saline solution. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

In other embodiments, the present invention provides a pharmaceutical composition comprising a cell in which an AAV provirus is integrated into the genome in a pharmaceutically-acceptable carrier or other medicinal agents, pharmaceutical agents, carriers, adjuvants, diluents, etc.

By "pharmaceutically acceptable" it is meant a material that is not biologically or otherwise undesirable, e.g., the material may be administered to a subject without causing any undesirable biological effects. Thus, such a pharmaceutical composition may be used, for example, in transfection of a cell ex vivo or in administering a viral particle or cell directly to a subject.

The present invention further provides a method of delivering a nucleic acid to a cell. For in vitro methods, the virus may be administered to the cell by standard viral transduction methods, as are known in the art. Preferably, the virus particles are added to the cells at the appropriate multiplicity of infection according to standard transduction methods appropriate for the particular target cells. Titers of virus to administer can vary, depending upon the target cell type and the particular virus vector, and may be determined by those of skill in the art without undue experimentation. Alternatively, administration of a parvovirus vector of the present invention can be accomplished by any other means known in the art.

Recombinant virus vectors are preferably administered to the cell in a biologically-effective amount. A "biologically-effective" amount of the virus vector is an amount that is sufficient to result in infection (or transduction) and expression of the heterologous nucleic acid sequence in the cell. If the virus is administered to a cell in vivo (e.g., the virus is administered to a subject as described below), a "biologically-effective" amount of the virus vector is an amount that is sufficient to result in transduction and expression of the heterologous nucleic acid sequence in a target cell.

The cell to be administered the inventive virus vector may be of any type, including but not limited to neural cells (including cells of the peripheral and central nervous systems, in particular, brain cells), lung cells, retinal cells, epithelial cells (e.g., gut and respiratory epithelial cells), muscle cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. Alternatively, the cell may be any progenitor cell. As a further alternative, the cell can be a stem cell (e.g., neural stem cell, liver stem cell). Moreover, the cells can be from any species of origin, as indicated above.

In particular embodiments of the invention, cells are removed from a subject, the parvovirus vector is introduced therein, and the cells are then replaced back into the subject. Methods of removing cells from subject for treatment ex vivo, followed by introduction back into the subject are known in the art. Alternatively, the rAAV vector is introduced into cells from another subject, into cultured cells, or into cells from any other suitable source, and the cells are administered to a subject in need thereof.

Suitable cells for ex vivo gene therapy include, but are not limited to, liver cells, neural cells (including cells of the central and peripheral nervous systems, in particular, brain cells), pancreas cells, spleen cells, fibroblasts (e.g., skin fibroblasts), keratinocytes, endothelial cells, epithelial cells, myoblasts, hematopoietic cells, bone marrow stromal cells, progenitor cells, and stem cells.

Dosages of the cells to administer to a subject will vary upon the age, condition and species of the subject, the type of cell, the nucleic acid being expressed by the cell, the mode of administration, and the like. Typically, at least about $10^2$ to about $10^8$, preferably about $10^3$ to about $10^6$ cells, will be administered per dose. Preferably, the cells will be administered in a "therapeutically-effective amount".

A "therapeutically-effective" amount as used herein is an amount of that is sufficient to alleviate (e.g., mitigate, decrease, reduce) at least one of the symptoms associated with a disease state. Alternatively stated, a "therapeutically-effective" amount is an amount that is sufficient to provide some improvement in the condition of the subject.

A further aspect of the invention is a method of treating subjects in vivo with the inventive virus particles. Administration of the parvovirus particles of the present invention to a human subject or an animal in need thereof can be by any means known in the art for administering virus vectors.

Exemplary modes of administration include oral, rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspensions in liquid prior to injection, or as emulsions. Alternatively, one may administer the virus in a local rather than systemic manner, for example in a depot or sustained-release formation.

In particularly preferred embodiments of the invention, the nucleotide sequence of interest is delivered to the liver of the subject. Administration to the liver may be achieved by any method known in art, including, but not limited to intravenous administration, intraportal administration, intrabilary administration, intra-arterial administration, and direct injection into the liver paraenchyma.

Preferably, the cells (e.g., liver cells) are infected by a recombinant parvovirus vector encoding a peptide, protein or therapeutic nucleic acid, the cells express the encoded peptide, protein or therapeutic nucleic acid and secrete it into the circulatory system in a therapeutically-effective amount (as defined above). Alternatively, the vector is delivered to and expressed by another cell or tissue, including but not limited to, brain, pancreas, spleen or muscle.

In other preferred embodiments, the inventive parvovirus particles are administered intramuscularly, more preferably by intramuscular injection or by local administration (as defined above). In other preferred embodiments, the parovirus particles of the present invention are administered to the lungs.

The parovirus vector disclosed herein may be administered to the lungs of a subject by any suitable means, but are preferably administered by administering an aerosol suspension of respirable particles comprised of the inventive parovirus vectors, which the subject inhales. The respirable particles may be liquid or solid. Aerosols of liquid particles comprising the inventive parovirus vectors may be produced by any suitable means, such as with a pressure-driven aerosol nebulizer or an ultrasonic nebulizer, as is known to those of skill in art. See, e.g. U.S. Pat. No. 4,501,729. Aerosols of solid particles comprising the inventive virus vectors may likewise be produced with any solid particulate medicament aerosol generator, by techniques known in the pharmaceutical art.

Dosages of the inventive parvovirus particles will depend upon the mode of administration, the disease or condition to be treated, the individual subject's condition, the particular virus vector, and the gene to be delivered and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^{13}$, $10^{14}$, $10^{15}$, $10^{16}$ transducting units or more, preferably about $10^8$ to $10^{13}$ transducting units, yet more preferably $10^{12}$ transducing units.

In particular embodiments of the invention, more than one administration (e.g., two, three, four, or more administrations) may be employed to achieve therapeutic levels of gene expression. According to this embodiment and as described above the humanized parvoviruses of the present invention are administered to circumvent neutralizing antibodies in the subject to be treated or to prevent the development of an immune response in the subject.

In summary, the parvovirus vectors, reagents, and methods of the present invention can be used to direct a nucleic acid to either dividing or non-dividing cells, and to stably express the heterologous nucleic acid therein. Using this vector system, it is now possible to introduce into cells, in vitro or in vivo, genes that encode proteins that affect cell physiology. The vectors of the present invention can thus be useful in gene therapy for disease states or for experimental modification of cell physiology.

The following examples are provided to illustrate certain embodiments of the invention. They are not intended to limit the invention in anyway.

Example 1

In the present example, the generation of AAV vectors that are covalently coated with HSA such that most or all antibody binding sites are masked is described.

Covalent Cross-Linking of Vector and HSA.

Appropriate cross linking agents have been developed and described to achieve attachment of two different proteins, and methods of use of such agents is well known to the skilled artisan. For example, certain heterobifunctional cross linking reagents could be used to form a covalent linkage between Cys34 of HSA with lysine residues that are present on the surface of purified AAV2. Heterobifunctional cross linking agents and methods of using the same are commercially available from Pierce. Covalent crosslinking of HSA to rAAV2 is advantageous in that the complexes, once formed, are stable.

AAV2-LacZ Preparation and Titering.

Recombinant AAV2 expressing the LacZ under the control of the CMV promoter was generated using helper virus free transient transfection of HEK293 cells and purified by combined cation exchange column chromatography and gradient centrifugation as previously described [Wright et al, 2006]. Vector purity was assessed by SDS-PAGE silver staining analysis. The AAV2-LacZ vector preparation used for these studies was highly pure as indicated by the presence of the expected viral capsid proteins VP1, 2 and 3, and absence of contaminating bands.

Conjugation of HSA to AAV2-LacZ.

The heterobifunctional cross linking reagent sulfosuccinimidyl 4[N-maleimidomethyl]cyclohexane-1-carboxylate (Sulfo-SMCC; Pierce, Rockford, Ill.) was used to crosslink cysteine 34 (Cys34) on HSA to lysine residues on the surface of AAV2-LacZ. Purified HSA (25% USP; Bayer) was dialysed into 0.10M sodium phosphate buffer, 0.30M NaCl, pH6.86 and then subjected to mild reduction with 5 mol DTT/mol HSA (Sogami et al 1984) in order to ensure reduction of Cys 34 without reduction of internal disulfide bonds (Peters, 1996). The reduction reaction was performed using the following two conditions: 1) 2.5 mM DTT+0.5 mM HSA (to give HSA $R_{Hi}$); and 2) 0.5 mM DTT+0.1 mM HSA (to give HSA $R_{Lo}$). The mildly reduced HSA's were dialysed into conjugation buffer composed of 100 mM sodium phosphate, 150 mM NaCl, pH 7.2 (PBS-CB) and adjusted to a stock concentration of 10 mg/mL with PBS-CB. Sulfo-SMCC crosslinking of HSA to AAV virus was performed using conditions recommended by the Pierce. Briefly, purified AAV2-LacZ was dialyzed into PBSC and passed through a MILLEX-GV 0.22 μm syringe filter (Millipore, Bedford, Mass.) to ensure removal of trace aggregates. The concentration of AAV2-LacZ was adjusted to $4\times10^{13}$ vg/mL (corresponding to 400 μg/mL). To 2 mL of AAV2-LacZ was added 0.2 mL of stock SulfoSMCC (4.8 mg/mL in sterile $H_2O$, prepared just prior to use), and the mixture incubated at 4° C. for 2 h. Following incubation the mixture was fractionated by 5300 size exclusion chromatography (Sepharcryl S300HR, Pharmacia, Sweden) to separate Sulfo-SMCC from vector particles. The AAV2LacZ-SulfoSMCC eluting at the void volume of the column was recovered at a concentration of (OD280 0.457). Two cross linking reactions were performed by mixing 0.8 mL of AAV2LacZ-SulfoSMCC with 0.2 mL of $HSAR_{Lo}$ or $HSAR_{Hi}$ and incubating the mixtures for 2 h at 4° C. Following incubation, the mixtures were fractionated on an S300 HR SEC column and fractions analyzed as described below. The putative vector-HSA conjugation products prepared using $HSAR_{Lo}$ and $HSAR_{Hi}$ are termed AAV2LacZ-$HSAR_{Lo}$ and AAV2LacZ-$HSAR_{Hi}$, respectively.

SDS-PAGE Analysis.

Column fractions obtained following SEC chromatography of cross-linked products were assessed analyzed by 8% or 4-12% gradient SDS-PAGE pre-cast gels (Invitrogen, Carlsbad Calif.). Silver staining of protein bands was performed using SilverXpress silver staining kit (Invitrogen, Carlsbad Calif.) using the manufacturer's protocols. SDS-PAGE analysis of the starting materials demonstrated that, in addition to the bands corresponding to AAV2 VP1, 2, and 3, and HSA, a new band migrating at approximately 130 kDa was observed in the HSA-conjugated vectors. This band is consistent with a covalent adduct between the most abundant AAV2 coat protein VP3 and HSA.

Dynamic Light Scattering.

Figure 6:
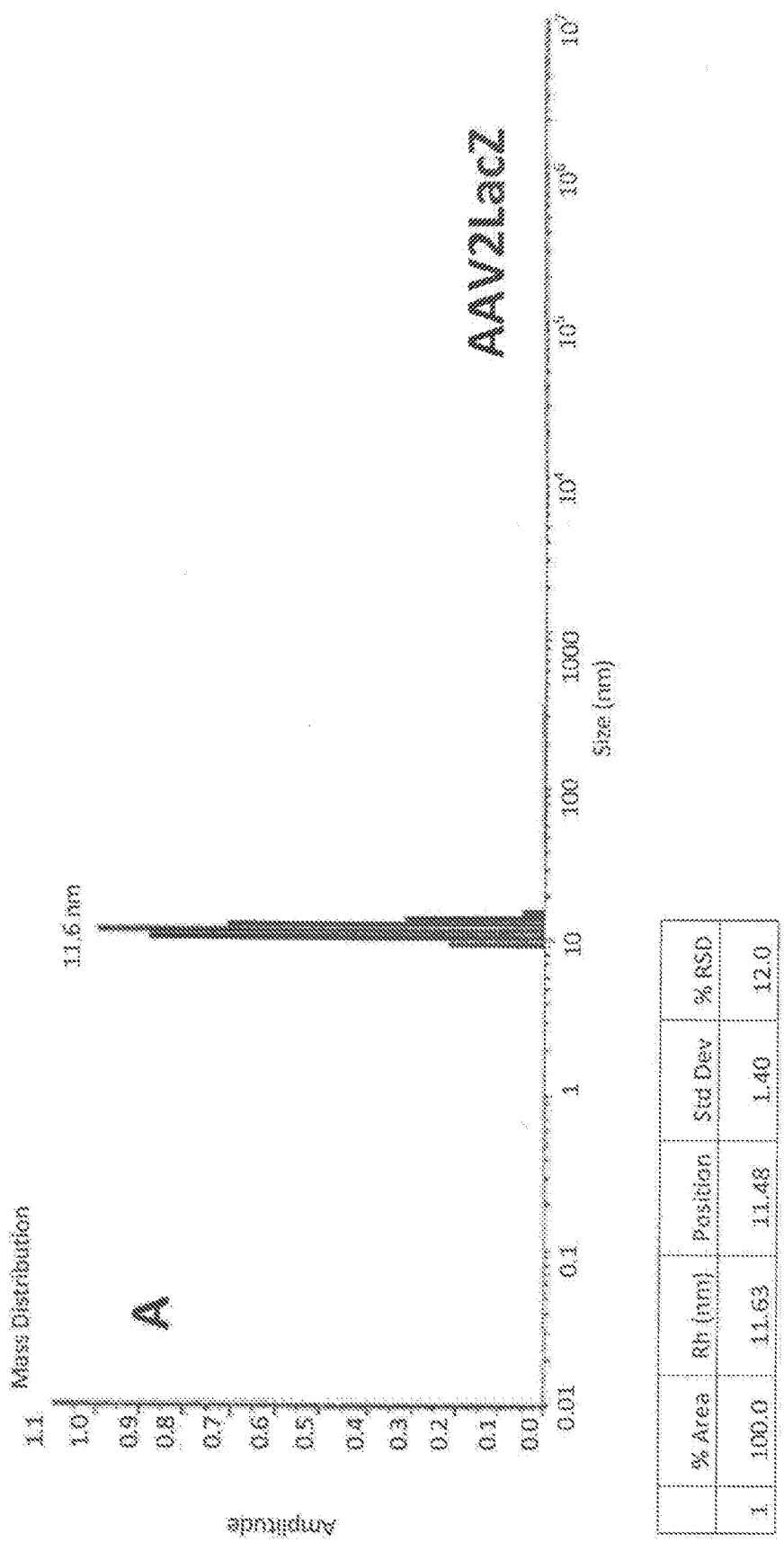
FIG. 6. Analysis by Dynamic Light Scattering (DLS) of unmodified and HSA-conjugated AAVLacZ. Samples of AAV2LacZ, AAV2LacZ-HSA/$_{RLo}$, or AAV2LacZ-HSA/$_{RHi}$ were subjected t by DLS analysis to measure the average particle radius in solution. Panel A shows DLS analysis results for highly purified AAV2LacZ vector alone. The average particle radius (shown on the X-axis, labeled 'Size (nm)', and in the accompanying table, labeled 'Rh (nm)') as measured by intensity of light scattering intensity is 11.6 nm, a size within the range consistent for AAV2 vectors using this method (Wright et al, 2005). Panel B shows DLS analysis results for purified AAV2LacZ-HSA/$_{RLo}$, which demonstrated an average particle radius of 16.6. Panel C shows DLS analysis results for AAV2LacZ-HSA/$_{RHi}$, which demonstrated an average particle radius of 18.3 nm. These results indicate that the HSA-conjugated AAV2LacZ particles have a larger average radius in solution, consistent with attachment and coating of the virus particles with HSA.
Figure 6:
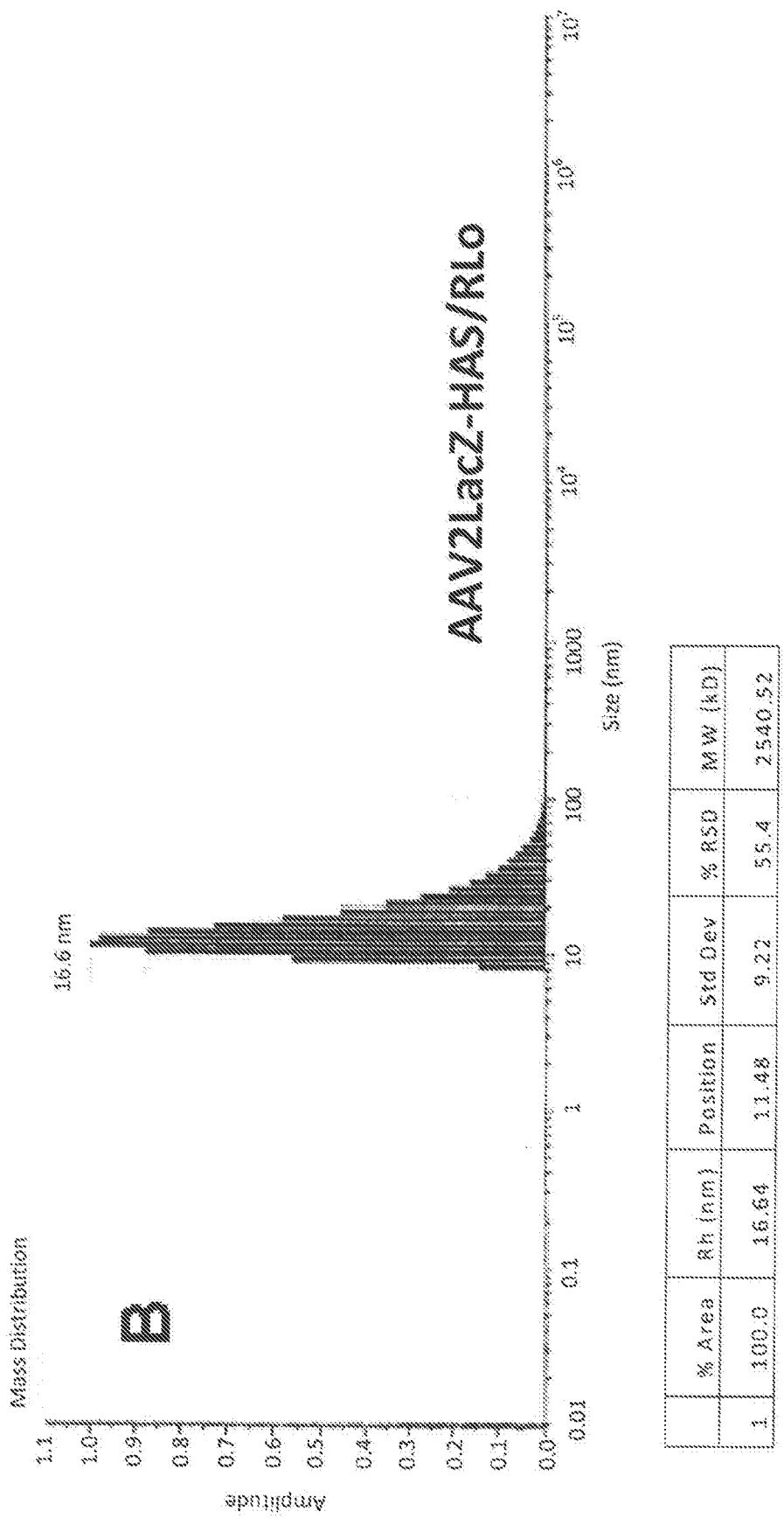
Figure 6:
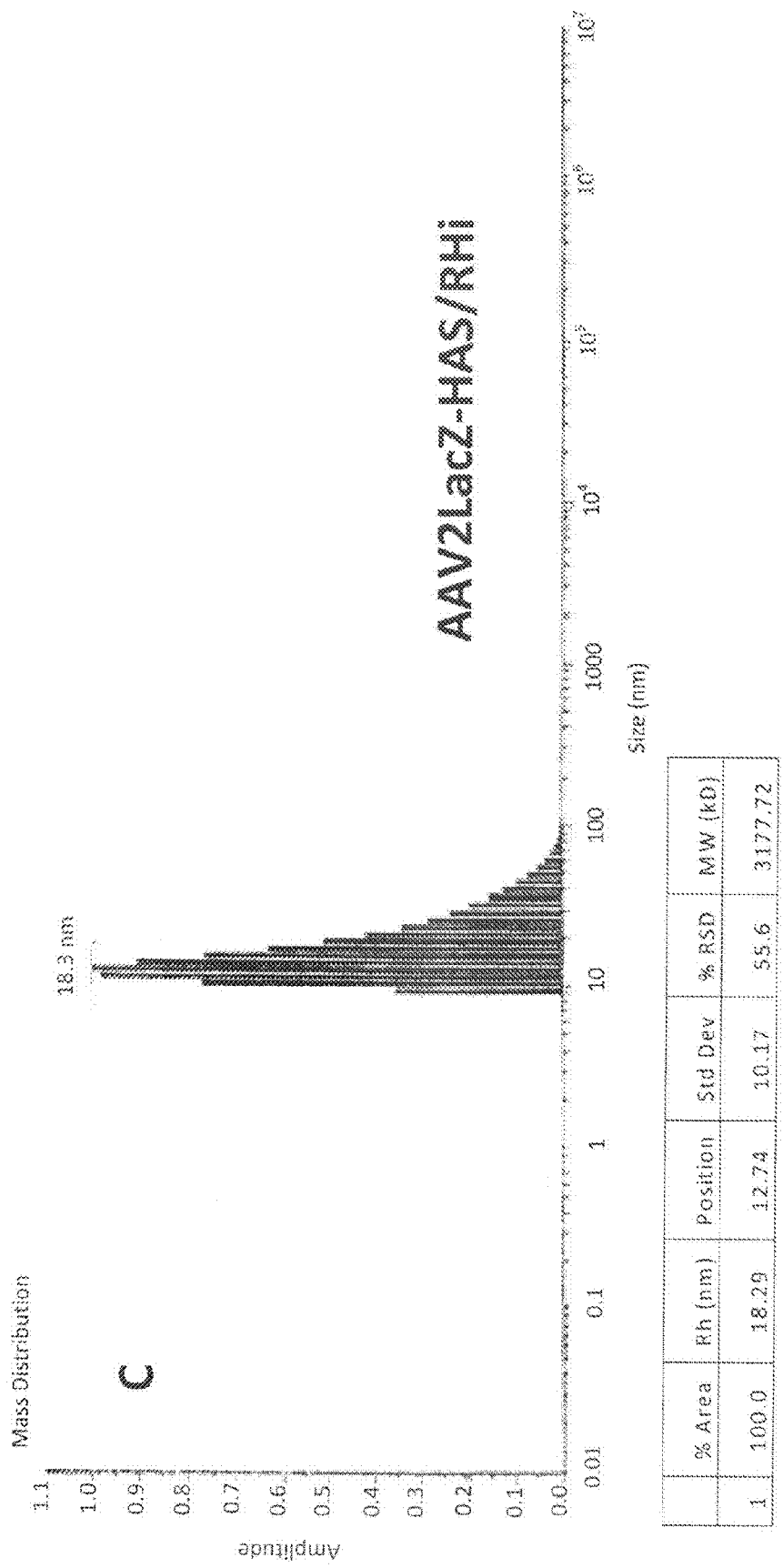
Figure 7A:
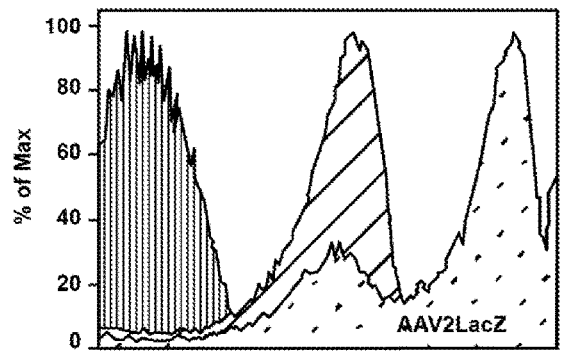
FIGS. 7A-7C. Analysis by flow cytometry of unmodified and HSA-conjugated AAVLacZ. AAV2LacZ (FIG. 7A), or vectors modified by covalent attachment of HSA (AAV2LacZ-HSA/$_{RLo}$ (FIG. 7B) and AAVLacZ-HSA/$_{RHi}$ (FIG. 7C) were diluted to the same concentration ($1\times10^{12}$ vg/mL) were incubated alone (Unstained), with secondary antibody only (Alexa Fluor 488 goat anti-mouse IgG (H+L); Invitrogen Molecular Probes, Eugene Oreg.) (Secondary antibody only (Anti-mouse FITC)), or with primary antibody (monoclonal antibody A20, AAV intact particle monoclonal MAB, Fitzgerald Industries International, Concord Mass.) followed by secondary antibody (Primary (A20)+ Secondary Antibodies). The highest binding of AAV specific monoclonal A20 was observed with AAV2LacZ, with lower antibody binding observed with the HSA modified vectors AAV2LacZ-HSA/$_{RLo}$ and AAV2LacZ-HSA/$_{RHi}$.
Figure 7B:
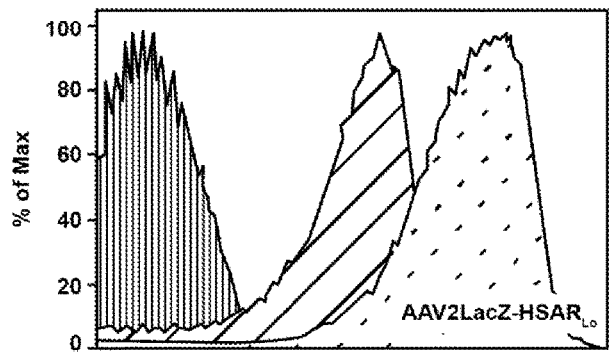
Figure 7C:
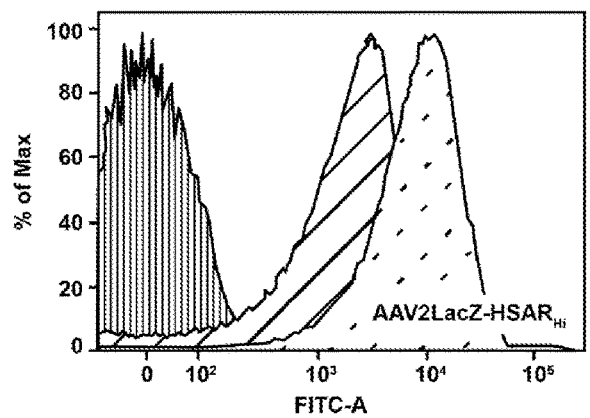
Figure 7C:
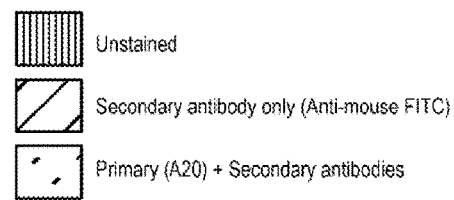

Samples of putative cross linked HSA-vector products were assessed by dynamic light scattering using a Viscotek Model 802 DLS apparatus. Twenty microliters of non-conjugated or HSA-conjugated AAV2-LacZ diluted to $1\times10^{12}$ vg/mL were added to a microcuvette. For each test article, data was obtained acquired for three independent runs, each involving 5 sequential 10 second acquisitions. Data were analyzed using OMNIsoft software using mass normalization to assess peak intensity, Rh (radius) and polydispersity. Dynamic light scattering was performed on unmodified and putative AAV2LacZ-HSA conjugates to approximate the average particle radius (Rh) in solution. As shown in FIG. 6, the average Rh value for AAV2LacZ was 11.6 nm, consistent with the radius of AAV2 as measure by crystallography and the expected variability of this assay method. The Average Rh values for AAV2LacZHSA/$R_{Lo}$ and AAV2LacZ-HSA/$R_{Hi}$ were 16.6 nm and 18.3 nm, respectively. Both of the HSA-conjugated vectors showed evidence of heterogeneous species corresponding to larger diameters, as evidenced by the tailing of the Size versus Amplitude plot in the direction of greater size values.

Flow Cytometry with Monoclonal Antibody A20.

Monoclonal antibody A20, which reacts with intact AAV2 capsid particles, was obtained from Fitzgerald Industries Inc (Concord Mass.). To a volume of 50 μL of unconjugated or HSA-conjugated AAV2LacZ adjusted to a concentration of $5\times10^{11}$ vg/mL diluted in phosphate buffered saline containing 1% FBS (PBS-FACS) was added 1 μL of stock monoclonal antibody A20 at a concentration of 50 μg/mL (Fitzgerald Industries, Concord Mass., and the mixtures incubated for approximately 30 min at 4° C. Tubes containing vectors without A20 were prepared in parallel. Then 50 μL of Alexa 488 goat anti-mouse antibody was added to tubes containing the various vectors with or without preincubation with A20. Tubes containing vectors without A20 and without the secondary antibody were prepared as controls. The tubes were incubated for approximately 30 min at 4° C. Finally 2504 of 4% paraformaldehyde prepared in phosphate buffered saline was added to all tubes, and incubated for approximately 10 min. The samples were then analysed on a Becton Dickinson FACS apparatus. The vector population was identified by forward and side scattering assessed on unlabeled samples (no primary (A20) or secondary antibodies) of unmodified and HSA-conjugated (modified) vectors. Vector incubated with secondary antibody only was included as an additional control for non-specific binding. As shown in FIG. 7, Panel A, specific binding of AAV2 capsid specific monoclonal antibody A20 to AAV2LacZ (red) was strongly positive, significantly higher than the secondary antibody only control (blue). Specific binding of A20 to AAVLacZ-HSA/$R_{Lo}$ (Panel B) and AAV2LacZ-HSA/$R_{Hi}$ (Panel C) was also positive, but weaker than that observed using the unmodified vector. The data support that conjugation of HSA successfully masked the viral epitopes recognized by A20 on the surface of the virus.

BiaCore Analysis.

Figure 8A:
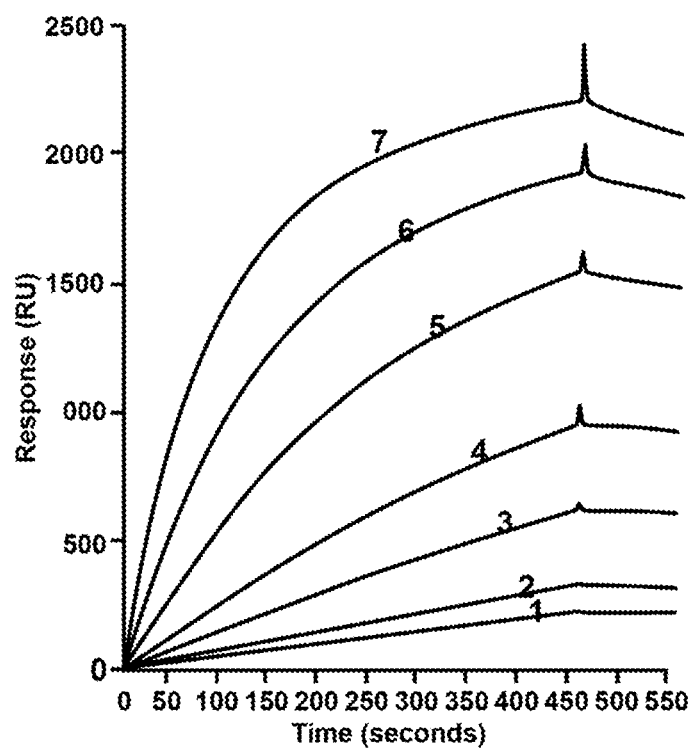
FIGS. 8A-8B. Analysis by Biacore of unmodified and HSA-conjugated AAVLacZ. AAV2LacZ, AAVLacZ-HSA/$_{RLo}$, and AAVLacZ-HSA/$_{RHi}$; were covalently bound to a three separate channels on a BIACORE CM % Sensor Chip using amine coupling according the manufacturer recommended protocol. The fourth available channel was subjected to the coupling protocol using HBS buffer only as a control. The estimated masses of AAV2LacZ, AAV2LacZ-HSA/$_{RLo}$, and AAV2LacZ-HSA/$_{RHi}$ attached to the respective channels were x, y, and z Response Units (RU). Following addition of AAV specific monoclonal antibody A20 at a concentration of 3.4 nM, association curves (FIGS. 8A-8B) and dissociation curves (FIG. 8A) of A20 binding to the immobilized vectors were measured. Shown in FIG. 8A, antibody A20 bound to a greater extent (higher Response as measure in RU) compared to the HSA modified vectors AAV2LacZ-HSA/$_{RLo}$ and AAV2LacZ-HSA/$_{RHi}$. Also shown in FIG. 8A, only a small fraction of A20 dissociated from AAV2LacZ after approximately 20,000 s of dissociation conditions (continuous flow of buffer over the chip) compared to almost complete dissociation of A20 from both AAV2LacZ-HSA/$_{RLo}$ and AAV2LacZ-HSA/$_{RHi}$ over the same time period.
Figure 8B:
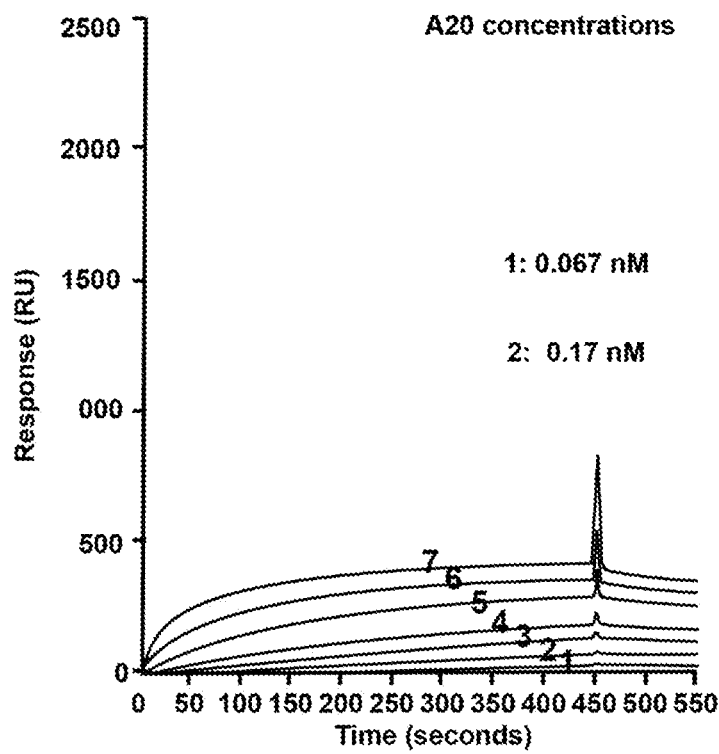
Figure 8:
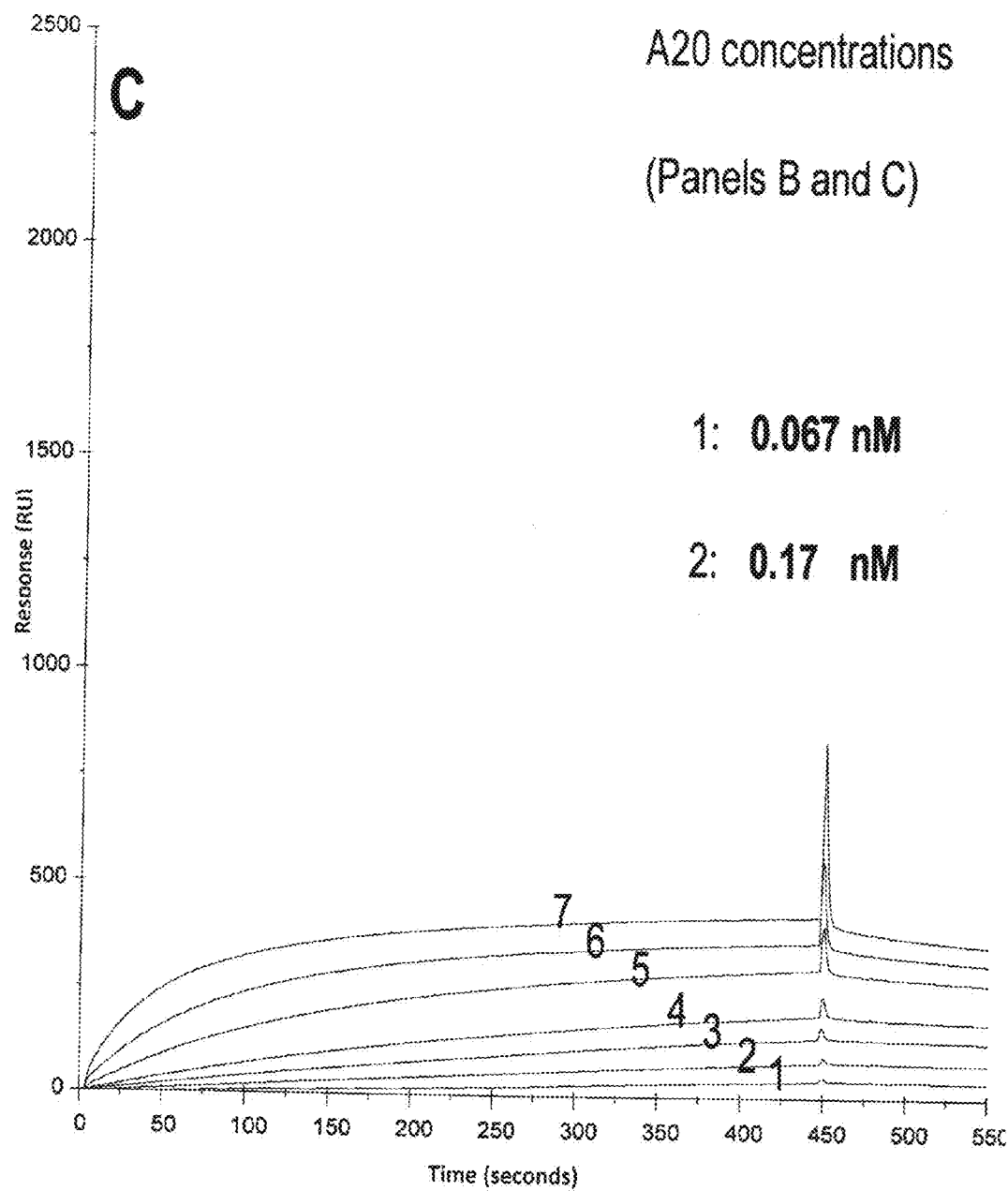

AAV2LacZ, AAVLacZ-HSA/$R_{Lo}$, and AAVLacZ-HSA/$R_{Hi}$ were covalently bound to a three separate channels on a BIACORE CM % Sensor Chip using amine coupling according the manufacturer recommended protocol. The fourth available channel was subjected to the coupling protocol using HBS buffer only as a control. Similar masses of AAV2LacZ and AAV2LacZ-HSA/$R_{Hi}$ attached, as assessed by a similar increase in the Response Units (RU) above the negative control. Following addition of AAV specific monoclonal antibody A20 at a concentration of 3.4 nM, association curves (FIG. 8, Panels A, B and C) and dissociation curves (Panel A) of A20 binding to the immobilized vectors were measured. Shown in Panel A, antibody A20 bound to a greater extent (higher Response as measure in RU) compared to the HSA modified vectors AAV2LacZ-HSA/$R_{Lo}$ and AAV2LacZ-HSA/$R_{Hi}$. Also shown in Panel A, only a small fraction of A20 dissociated from AAV2LacZ after approximately 20,000 s of dissociation conditions (continuous flow of buffer over the chip) compared to almost complete dissociation of A20 from both AAV2LacZ-HSA/$R_{Lo}$ and AAV2LacZ-HSA/$R_{Hi}$ over the same time period. Panel B shows the A20 association curves, provided at concentration ranging from approximately 0.067 nM to 6.7 nM, to immobilized AAV2LacZ. Panel C shows the A20 association curves using the same A20 concentration range and timeframe, to AAV2LacZ-HSA/$R_{Hi}$. These data support the presence of fewer A20 binding sites on the HSA-conjugated vectors compared to unmodified AAV2LacZ, and support that the binding affinity of A20 binding to the HSA-conjugated vectors is lower than the binding affinity of A20 binding to unmodified AAV2LacZ.

Transduction and In Vitro Neutralization by Monoclonal Antibody A20

Figure 9:
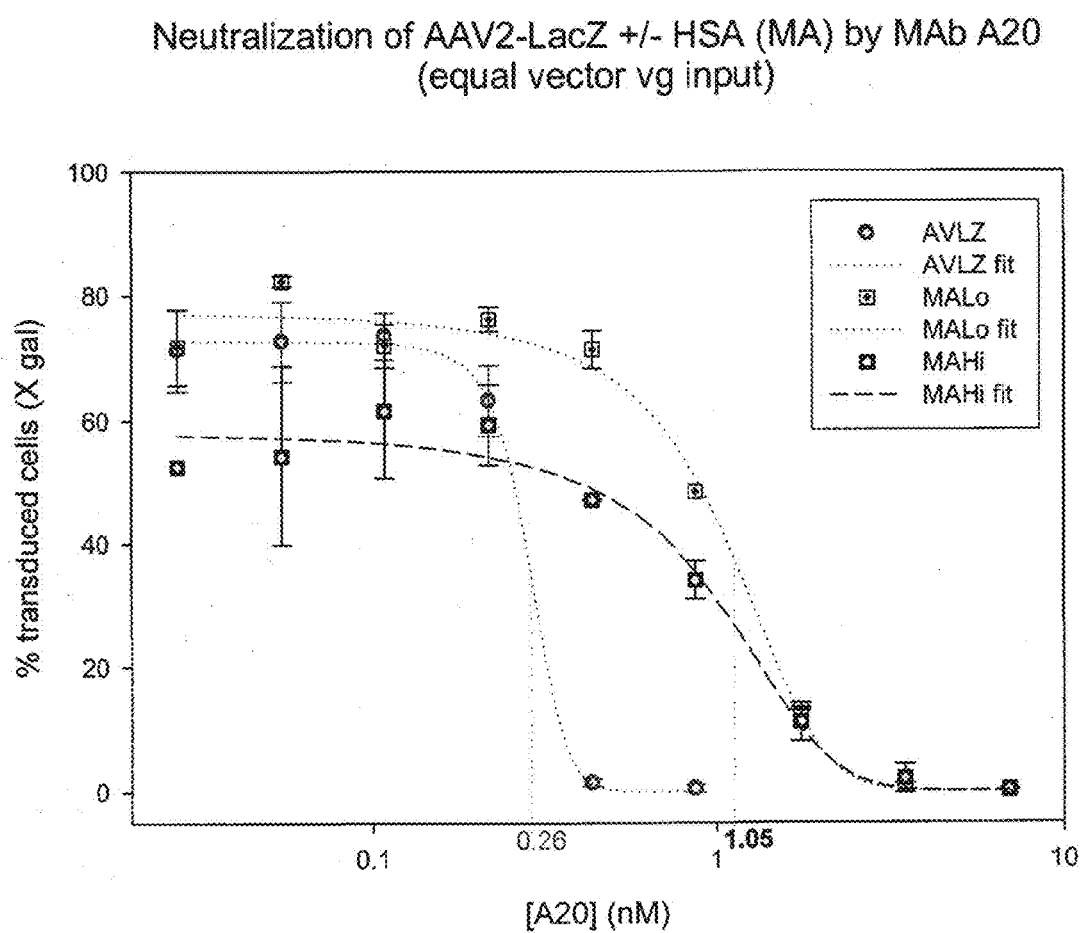
FIG. 9. Increase resistance of HSA-conjugated AAVLacZ to neutralization by AAV-specific monoclonal antibody A20. A fixed concentration ($1\times10^{11}$ vg/mL) of AAV2LacZ (AVLZ), AAV2LacZ-HSA/$_{RLo}$ (MALo), or AAV2LacZ-HSA/$_{RHi}$ (MAHi), was first pre-incubated with two-fold serial dilution of monoclonal antibody A20 for 1 h at 37° C., and then the mixtures transferred to HepG2 cells growing in 96 well cell culture plates. While unmodified AAV2LacZ vector was 50% neutralized by A20 at an antibody concentration of 0.26 nM. In contrast, both HSA-conjugated AAV2LacZ variants were approximately 4-fold more resistant to neutralization, requiring A20 at 1.05 nM for 50% neutralization.

To assess susceptibility to neutralization by mAb A20, a fixed vector concentration ($1 \times 10^{11}$ vg/mL) was first pre-incubated with two-fold serial dilution of monoclonal antibody A20, and the mixture then added to HepG2 cells. As shown in FIG. 9, unmodified AAV2LacZ vector was 50% neutralized by A20 at an antibody concentration of 0.26 nM. In contrast, both HSA-conjugated AAV2LacZ variants exhibited 4-fold more resistant to neutralization, requiring A20 at 1.05 nM for 50% neutralization. When normalized to transducing units, AAV2LacZ-HSA$_{RLo}$ and AAV2LacZ-HSA$_{RHi}$ were 16-fold and 68-fold greater resistance to neutralization by A20. At the input concentration of vector chosen, AAVLacZ and AAV2LacZ-HSA$_{RLo}$ demonstrated similar transduction levels in the absence of A20 (70-80%); however, AAV2LacZ-HSA$_{RHi}$ demonstrated slightly lower transduction (50-60%).

Example 2

In this example, the generation of AAV vectors that are modified with an AAV binding ligand such that most or all antibody binding sites are masked is described.

Covalent attachment of an AAV2 binding ligand, such as heparin to HSA is performed. HSA can be modified by attaching a ligand that is known to bind to the surface of AAV2 vectors (e.g., heparin). It is known that AAV2 has binding sites for heparin (60 sites per AAV2 particle). Thus, covalent attachment of heparin to purified HSA can be achieved such that one HSA molecule has one attached heparin molecule. It is most preferable that only one heparin molecule be attached to each HSA molecule, because attachment of 2 or more heparin molecules per HSA would lead to HSA derivatives that would be expected to bind more than one vector particle and thereby lead to vector aggregation. Therefore attachment of heparin to a unique site (e.g. Cys34) on HSA provides a suitable mono-heparin HSA derivative to generate the huAAV2 vectors described herein. Mono-heparin HSA is then incubated with purified AAV2 vectors to allow binding of the mono-heparin HSA to AAV2 vectors via the 60 heparin binding sites on the vector. An advantage of this strategy is that both HSA and heparin are available in highly purified forms and abundant quantities are available at reasonable costs. Additional details of a protocol to generate humanized AAV2 vectors are given below:

Example of Preparation of HSA-Cys34-Heparin (Mono-Heparin HSA) (Also Referred to as MAKH-LN; or MALN):

It is generally known that the only non-disulfide bonded Cys residue in native HSA is Cys34 (Peters, 1996). Molecular cross linking to Cys34 provides a method to attach a single ligand molecule per molecule of HSA. The objective of these experiments was to make human serum albumin (HSA) containing a single heparin moiety attached at Cys 34 (HSA-Cys34-Hep: variously referred to in other parts of this document as MALN; MAKM-LN; and mono-heparin HSA).

To this end, 25% Albumin (HSA) (Bayer, Lot26N29J1) was dialyzed against 0.1M sodium phosphate, 0.3M NaCl, pH 6.86. The HSA was then treated with dithiothreitol (DTT) at a molar ratio of 5 mol DTT/1 mol albumin at room temperature, conditions known to reduce Cys34 but not break other disulfide bonds in the HSA molecule. The resulting mercapto albumin (MA) was then dialysed into 0.1M sodium phosphate, 0.15M sodium phosphate, pH7.

The heterobifunctional cross linking reagent KMUH (product 22111, Pierce Biotechnology products) was purchased. KMUH was used to derivatize Cys34 of MA according to the instructions provided by Pierce. Approximately 10 mol KMUH per mol MA was mixed together per manufacturer's instructions. The derivatized MA, referred to herein as MAKM, predicted to have the KMUH maleimide group coupled to MA Cys34, was then dialyzed into 0.1M sodium acetate buffer, pH 5.5 (SAB). Concurrently, Lovenox (100 mg/mL low molecular weight heparin manufacture by Aventis; Lot 1C043) was oxidized using sodium meta periodate, the reaction stopped with glycerol, and the mixture dialyzed against sodium acetate buffer. The oxidized Lovenox is termed LN.

MAKM was mixed with LN at varying ratios, specifically, the ratio of MAKM to LN was varied from 2:1 to 1:5 in independent reactions. The hydrazide group on MAKM should form a covalent bond with oxidized carbohydrate groups on LN, thereby resulting in the formation of MAKM-LN. After reaction, the material was dialyzed extensively to remove non-complexed LN, and for some confirmatory experiments the mixture was further subjected to size exclusion chromatography (sephacryl 100) to completely remove unbound LN from MAKM-LN. The name MAKM-LN was further abbreviated to MALN.

Figure 10:
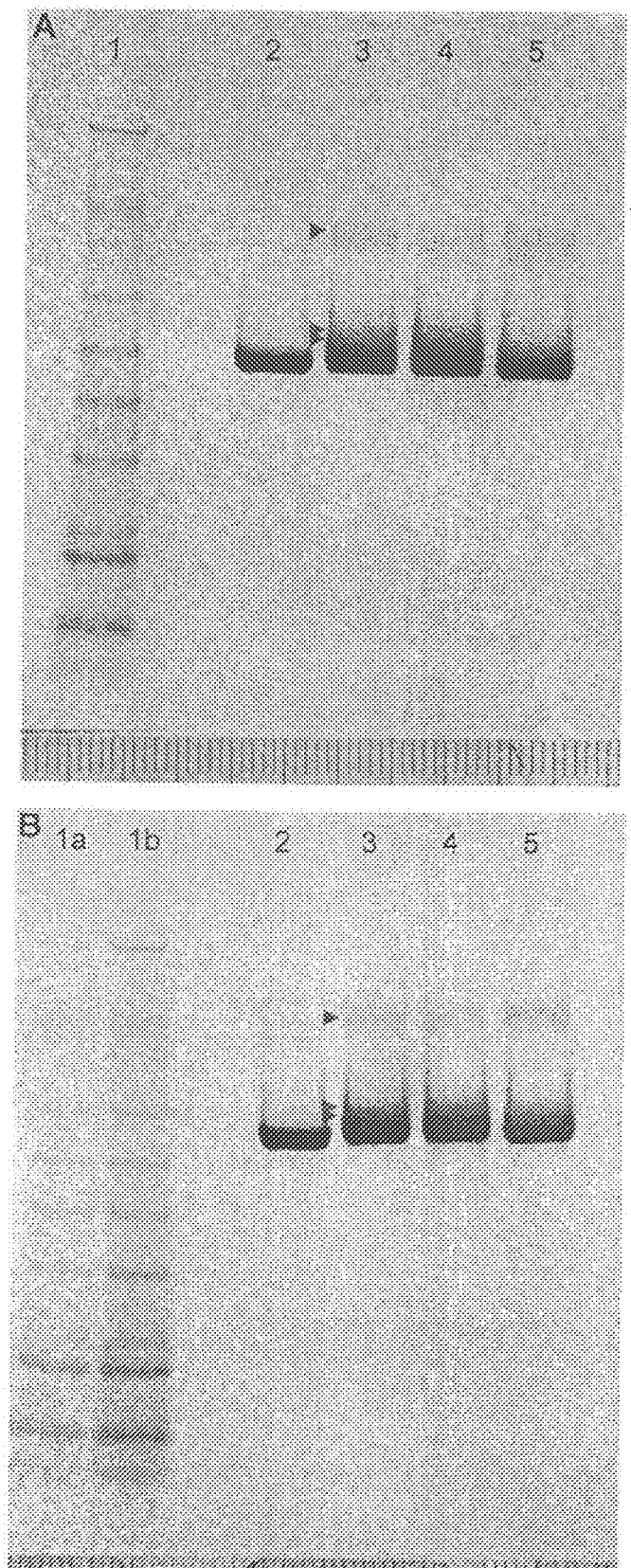
FIG. 10. Molecular conjugates of human serum albumin with heparin—crosslinking of HSA and heparin at HSA Cys34 are shown. Molecular conjugates of HSA (Plasbumin-25 (Bayer), a human parenteral grade of HSA) and heparin (Lovenox (Aventis), a human parenteral grade heparin) were prepared as described in Materials and Methods. The conjugates are referred to as MALN, a conjugate of mercaptoalbumin (MA) and lovenox (LN). The conjugates were analyzed by SDS-PAGE, representative results of which are shown in Panel A (non-reducing conditions) and B (reducing conditions). In Panel A, Lane 2 shows HSA that has been treated with cross-linking reagent KMUH (MAKM, which comprises mercapto albumin plus the cross-linking reagent) in the absence of LN. The 60 kDa albumin band is clearly observed. The band is tight, showing homogeneity in the MAKM molecular population. Lane 3 shows the results of the 1:1 mixture of MAKM and LN (1×). Two features are present that differentiate Lane 3 material from MAKM only (Lane 2): 1) there appears to be material of molecular weight (Mr) slightly greater than the approx 60 kDa of MAKM, i.e. there is a broadening of the albumin band to slightly higher Mr species, this higher Mr material diffusing into a 'smear' of material above the expected position of MAKM (green arrows); and 2) there is a higher Mr band that may correspond to a dimer of MAKM (red arrow). Lane 4, in which the conjugation reaction contained 2×LN, was not distinguishable from the material in Lane 3. Lane 5, in which the final conjugation reaction contained 5× less LN, did show a difference from Lanes 3 and 4, namely the broadening of the higher Mr (top) side of the dense MAKM band was significantly less. The albumin band in Lane 5 was intermediate in appearance between the MAKM (Lane 2) and the putative MALN species in Lanes 3 and 4. As shown in Panel B, similar results were observed when the samples were analyzed under reducing conditions.

The MALN conjugates were analyzed by SDS-PAGE, representative results of which are shown in FIG. 10, Panels A and B. Panel A, (non-reducing conditions), Lane 2 shows MAKM which was not allowed to react with LN. The 60 kDa albumin band is present. The band is tight, showing homogeneity in the MA population. Lane 3 shows the results of the 1:1 mixture of MAKM and LN. Two features are present that differentiate Lane 3 material from the MAKM (Lane 2): 1) there appears to be material of molecular weight (Mr) marginally greater than the approx 60 kDa of MAKM, i.e. there is a broadening of the albumin band on the higher Mr (top) side, this higher Mr material diffusing into a 'smear' of material above the expected position of MAKM (green arrows); and 2) there is a higher Mr band possibly corresponding to a dimer of MAKM (red arrow). Lane 4, in which the final conjugation reaction contained 2× more LN, was not distinguishable from the material in Lane 3. Lane 5, in which the final conjugation reaction contained 5× less LN, did show a difference from Lanes 3 and 4, namely the broadening of the higher Mr (top) side of the dense MAKM band was significantly less. The albumin band in Lane 5 was intermediate in appearance between the MAKM (Lane 2) and the putative MAKM-LN species in Lanes 3 and 4. Similar results were observed when the samples were analyzed under reducing conditions (note the lane numbering is different in Panel B, but sequence of samples is the same).

Figure 11:
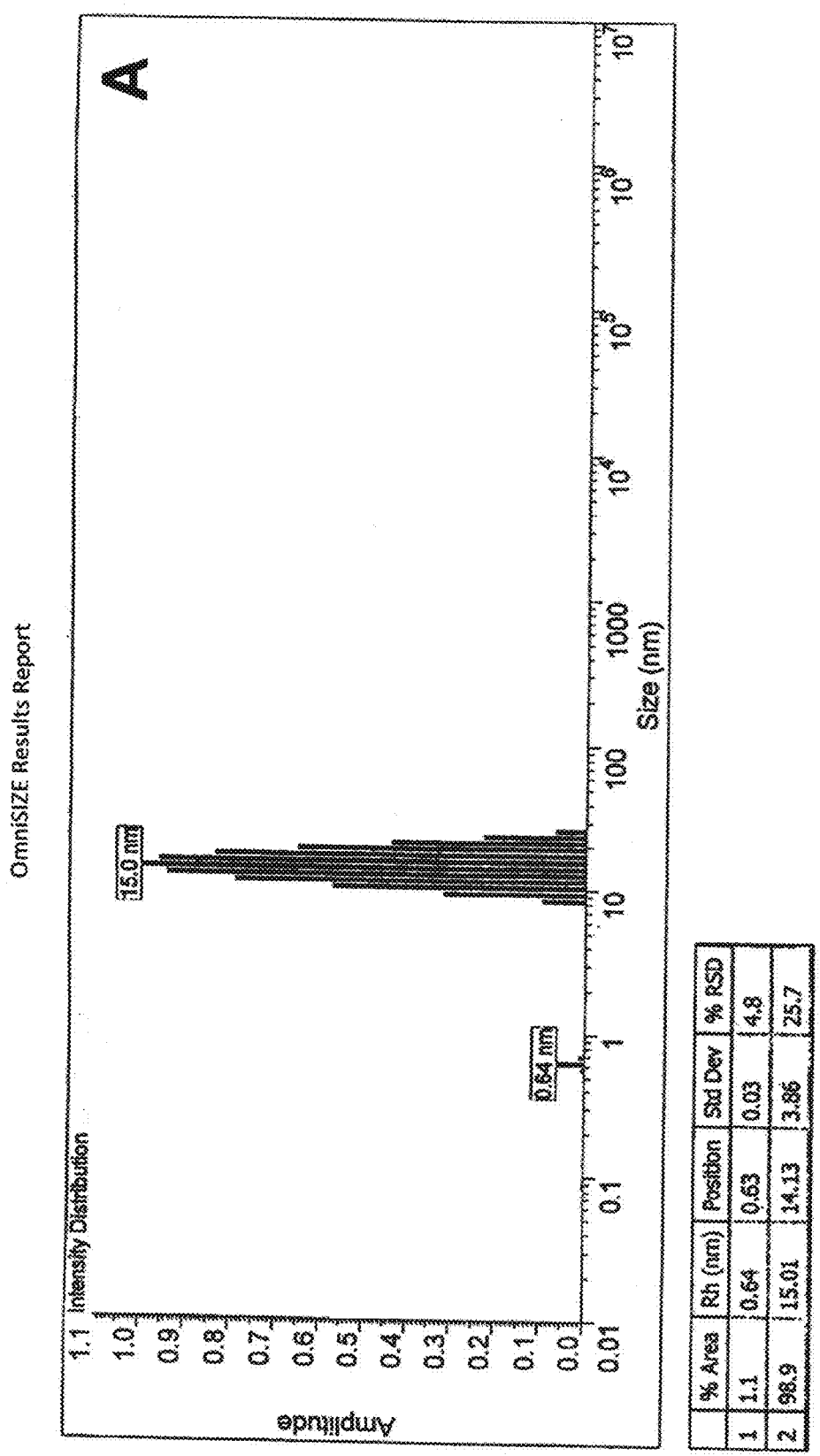
FIG. 11. Demonstration of binding of AAV2 vector with MALN by dynamic light scattering. Dynamic light scattering (DLS) is capable of providing information about the size of microscopic species, and can therefore provide evidence that a particle of known size (e.g. an AAV2 virus particle, having a radius typically measured in the range 12-15 nm) has interacted with another particle(s) that would be expected to change the average measured radius. DLS measurements can be performed directly on solutions of proteins and virus/vectors without interfering with the natural interactions that occur between these molecular species. Panel A shows DLS analysis of highly purified AAV2-LacZ vector alone. The average particle radius (shown on the X-axis, labeled 'Size (nm)', and in the accompanying table, labeled 'Rh (nm)') as measured by intensity of light scattering intensity is 15.0 nm, a size within the range consistent for AAV2 vectors using this method (Wright et al, 2005). Panel B shows DLS analysis of the same purified AAV2-LacZ vector after it was incubated for approximately 2 h with MALN and then purified by size exclusion chromatography. Two major peaks are observed in Panel B: 1) the peak at 3.7 nm corresponds to MALN (possibly monomers and/or multimer); and 2) the peak at 23.2 nm corresponds to AAV2-LacZ that has been coated with MALN and therefore exhibits a greater average radius compared to AAV2-LacZ alone. Minor peaks in both panels are also observed (<1 nm) and likely correspond to background.
Figure 11:
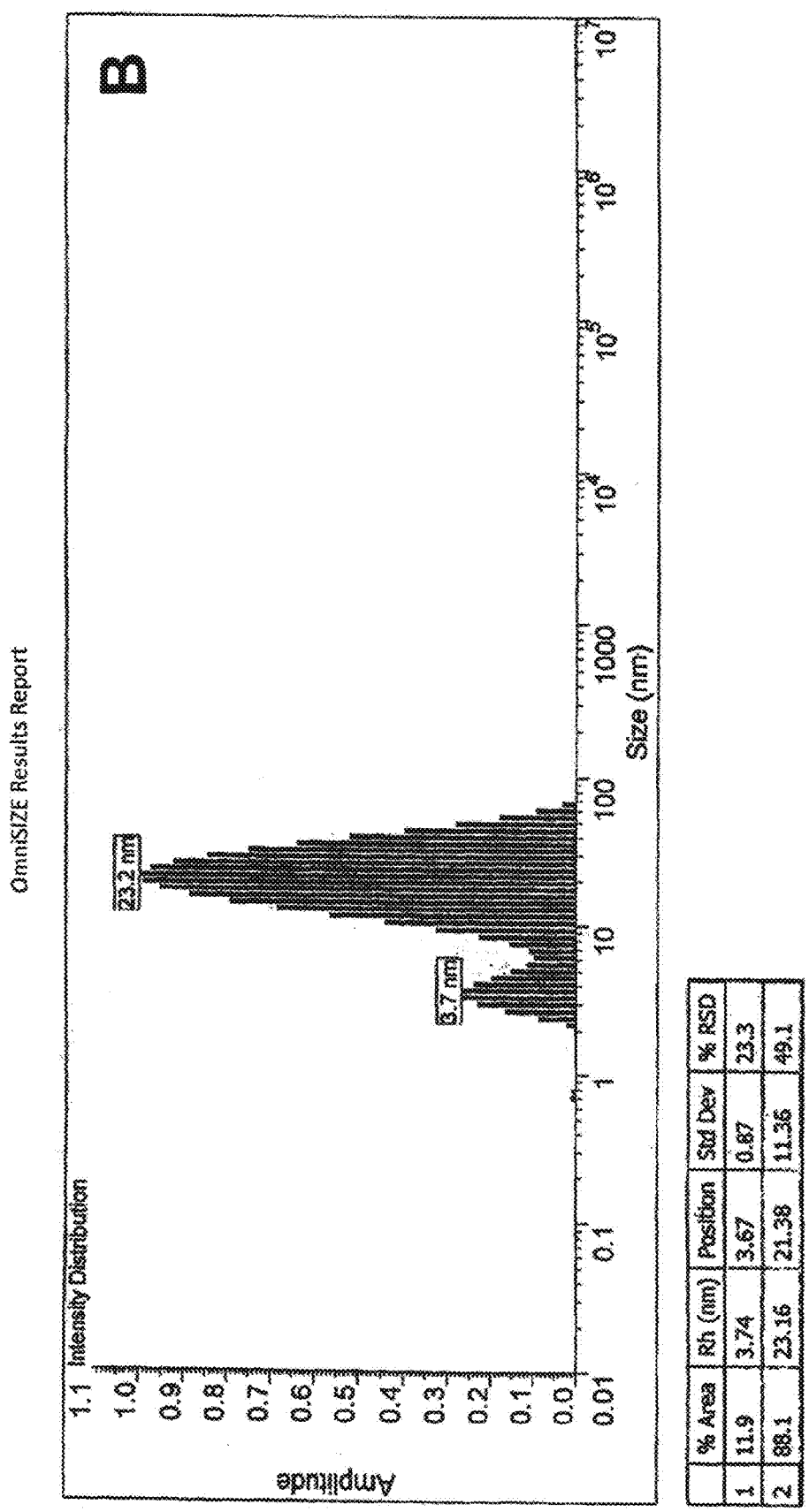
Figure 12:
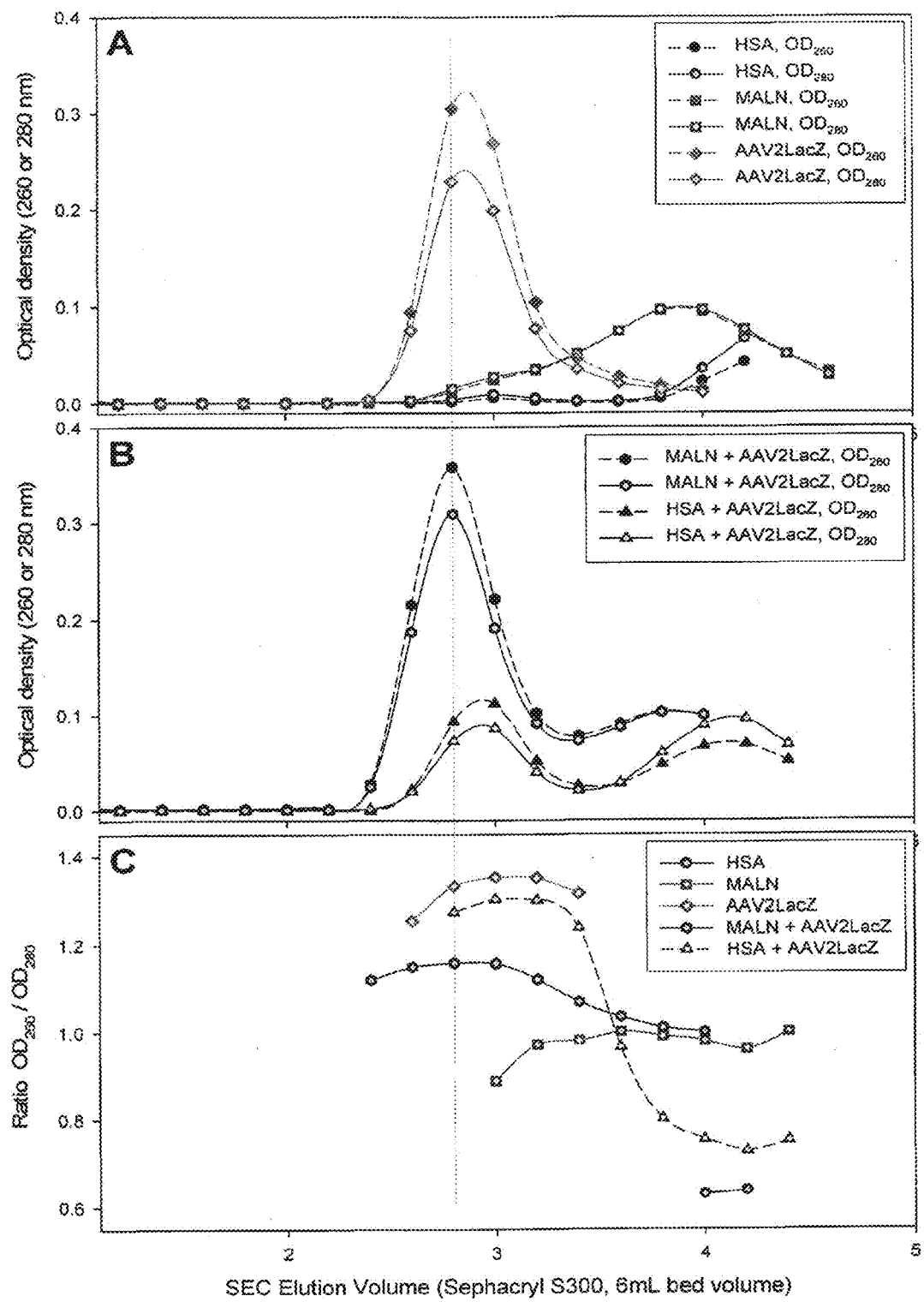
FIG. 12. Demonstration of binding of AAV2 vectors with human serum albumin coupled to heparin (MALN) by size exclusion chromatography. HSA alone, MALN alone, or AAV2LacZ alone were applied to a ~6 mL bed volume size exclusion chromatography (SEC) column (Sephacryl S300 resin). After sample application to the column, 254 μL fractions were collected and analyzed by optical density measurement at 260 nm and 280 nm. Panel A: the AAV2LacZ (alone) peak eluted at ~2.9 mL elution volume, MALN (alone) was eluted at ~3.8 mL elution volume, and the HSA (alone) eluted at ~4.2 mL. Panel B: samples containing AAV2LacZ mixed with HSA or MALN, in which $OD_{280}$ extinction was contributed equally from the AAV2LacZ vector and the protein (HSA or MALN), were mixed and incubated overnight at approximately 4° C. The sample containing HSA incubated with AAV2LacZ was resolved into two peaks of approximately equal peak heights, the first eluting at ~2.9 mL (similar to AAV2LacZ alone shown, Panel A) and the second eluting at ~4.2 mL (similar position to HSA alone, shown in Panel A). In contrast the sample containing MALN incubated with AAV2LacZ was resolved into two peaks of significantly different peak heights, the larger peak eluting first at ~2.8 mL, and the smaller second peak eluting at ~3.8 mL (similar to MALN alone as shown in Panel A). Analysis of the ratio of $OD_{260}$ to $OD_{280}$ for fractions eluted following SEC of the various mixtures is shown in Panel C. The $OD_{260}/OD_{280}$ for MALN starting material was approximately 1.0, and the predetermined $OD_{260}/OD_{280}$ for the AAV2LacZ vector starting material was approximately 1.4. The $OD_{260}/OD_{280}$ ratio of material in the larger (first) peak (which corresponded approximately to the expected elution position for AAV2LacZ) following SEC analysis of AAV2-LacZ pre-incubated with MALN was approximately 1.15. The decreased $OD_{260}/OD_{280}$ ratio relative to the value expected for pure AAV2LacZ supports that MALN bound to AAV2LacZ, forming a complex. MALN alone would not be expected to elute at this elution volume.

The likely explanation for the high Mr broadening in MAKM-LN containing lanes compared to MAKM alone is the formation of adducts of heparin to albumin. The predicted species based on the heterobifunctional cross linking reagent used (KMUH) and the procedure used is albumin cross linked to low molecular weight heparin via Cys34. The slight increase in the Mr of MAKM-LN (average MAKM-LN is approximately 5 k larger than MAKM) is consistent with the average size of low molecular weight heparin in Lovenox (4.5 kDa). The lack of a distinct band at approximately 65 kDa is consistent with the size heterogeneity in Lovenox, which is a mixture of heparin species ranging widely in Mr, with approximately 70% in the range from 2000 to 8000 Da, and the remainder of even higher or lower Mr. The experimental data shown in FIG. 11, Panels A and B is consistent with covalent attachment of low molecular weight heparin of broad size heterogeneity (ranging primarily from 2-8 kDa) at Cys34 of albumin.

The band at approximately 130 kDa likely results from the formation of MAKM dimers. Although a faint species at approx 110 kDa is observed in the MAKM alone lane, the stronger putative MAKM dimer is of distinct Mr and stronger intensity. The dimer is likely formed because the oxidized LN has many reactive groups that can interact with reactive hydrazides attached to MA Cys34. Therefore one would predict that dimers would occur in which one LN reacts with two MAKM molecules. The lack of higher Mr species (trimers, etc.) is evidence that Cys34, present at only one copy MA molecule, is the species that has been derivatized with KMUH. If other moieties in albumin were involved in cross linking, one would predict a range of dimers, trimers and higher oligomers of albumin.

The reduced albumin band broadening in MAKM-LN (5:1) (Lane 5 in FIG. 10, Panels A and B) compared to the MAKM-LN (1:1 or 1:2)) was likely observed because the reaction that occurs in the presence of less than an optimal ratio of LN to MAKM (i.e. when LN<<MAKM) is less efficient in forming the desired MAKM-LN (monomer) product.

Formation of huAAV by Mixing of AAV2 Vector with MALN as Assessed by Dynamic Light Scattering:

The MALN was dialysed against PBS. Preliminary experiments were then performed to assess interaction of MAKM-LN with recombinant AAV2 by dynamic light scattering (DLS). MALN is preferable as it may coat AAV2 vectors in a reversible manner, reducing or preventing binding of anti AAV antibodies, and thereby improve the ability to delivery predictable amounts of vectors in vivo (for example into human subjects who often have pre existing AAV antibodies). Interaction between AAV2 and HSA-Cys34-Hep (aka MALN) is predicted to occur by binding of HSA-Cys34-Hep to heparin binding sites distributed on the surface of AAV.

For the dynamic light scattering experiments, all reagents were filtered through a 0.2 micron filter before use. AAV2-hFIX16 in neutral buffered saline was first assessed by dynamic light scattering as a control (FIG. 11, Panel A). Twenty microliters of the vector at a concentration of approximately $1\times10^{13}$ vg/mL gave a light scattering intensity of approximately 1500 k counts and size analysis indicated 98.9 percent radius (Rh)=15.01 nm, and 1.1% Rh=0.64 nm. The approx Rh=15 nm corresponds to vector. In FIG. 6, Panel B is shown the result when recombinant AAV2 and MALN were mixed together. Assessed after ten minutes incubation at room temperature, the light scattering intensity was approx 2000 k counts, and size analysis indicated 12% of a species at Rh=3.74 nm, and 88% of a species at Rh=23 nm. These data are consistent with the interaction of MALN monomers with AAV2 particles to form a 'coated' AAV2 particle of Rh=23 nm. Note that most of the light scattering intensity (83%) is expected to be contributed to by the AAV2 particles, or slightly modified, larger MAKM-LN coated versions of the AAV2 particle.

Formation of huAAV by Mixing of AAV2 Vector with MALN as Assessed by Size Exclusion Chromatography:

Experiments were performed to assess the interaction of AAV2-LacZ vector with MALN by size exclusion chromatography (SEC). AAV2-:LacZ was assessed alone, or after mixing an incubation for approximately 2 h at room temperature with HSA, or with MALN. The SEC elution profile of HSA and MALN alone were also assessed as controls. The results, providing evidence of a species composed of AAV2-LacZ bound to MALN (as evidenced by identification of a species equal to or slightly larger than AAV2-LacZ with a decreased $OD_{260}/OD_{280}$ ratio (FIG. 12, Panels B and C) compared to AAV2-LacZ, are summarized in the brief description of FIG. 12.

The strategy and approaches described may be used to 'humanize' other virus-based vector particles, such as those based on adenoviruses, herpesviruses, lentiviruses, and other viruses. For example, a heparin binding site may be engineered into a virus of interest, and then albumin monosubstituted with heparin added to the recombinant virus to coat the surface. Furthermore, techniques such as site-directed mutagenesis of vector capsid sequences may performed on viral vectors known to contain a heparin binding site to beneficially modify (increase or decrease) the affinity of binding of albumin monosubstituted with heparin in order in order to optimize the coating of the vector with albumin or other human molecules. Albumin substituted with heparin may have other uses based on the fact that, unlike albumin with more that one heparin or similar moiety per albumin molecule, it will not cause aggregation of particles to which it binds.

Example 3

In an alternative approach, modification of the vector surface by attaching small ligands to the vector surface that are known to bind HSA may be employed. AAV2 vectors derivatized with such ligands could be mixed with HSA, which would then bind in a non-covalent manner. For example, it is known that HSA has a high affinity binding site for certain fatty acids (reviewed in Peters (1996)). Fatty acids could be covalently attached to the surface of AAV2 vectors, and the vectors then incubated with purified HSA under conditions to allow non-covalent binding of HSA to the fatty acids molecules. For example, acylation of the epsilon amino groups of lysine residues to attach long fatty acyl residues to proteins has been described (Plou et al. (1994)). To make huAAV2 vectors using this strategy, long chain fatty acids (eg. palmitoyl chloride) or other relevant fatty acid like molecule could be attached covalently to some (or all) of the approximately 420 Lys residues that are exposed on the surface of AAV2. The poly-acylated AAV vector could then be mixed with HSA. Upon incubation, HSA molecules are predicted to bind (noncovalently) to fatty acid molecules attached to the vector, and coat the vector with HSA. An advantage of this strategy is that only the vector is chemically modified, and the HSA, which could be purified from the prospective subject, or be a commercial, parenteral grade, is not modified.

Example 4

The following prophetic example describes the clinical administration of humanized AAV vector. AAV2 expressing human coagulation factor IX (hFIX) under the control of a hepatocyte specific promoter (e.g. Manno et al, 2006) can be manufactured using methods appropriate to ensure purity and quality as required for clinical (human) administration. The purified AAV2-hFIX vector, adjusted to a concentration of approximately $1 \times 10^{13}$ vg/mL can be incubated with mono-heparin substituted human serum albumin adjusted to a concentration in the range 0.1 to 1 mg/mL, prepared by a method similar to that described in Example 1 using components and process appropriate to ensure purity and quality as required for clinical administration. After incubation to allow binding of mono-heparin HSA molecules to AAV2-hFIX vector particles, an initial dose (approximately $1 \times 10^{12}$ vg/kg) of the resulting 'huAAV2-hFIX' vector may be administered to a human subject who has severe hemophilia B and who has been previously determined to have significant levels of circulating antibodies to AAV2 (a titer of approximately 1:100). The vector may be administered via a peripheral vein (e.g. administration to a vein in the subject's arm or leg) or into a blood vessel that leads directly into the subject's liver (e.g. hepatic artery or portal vein). Following administration, the huAAV2-hFIX vector can transfer the hFIX gene to liver hepatocytes. The subject will then be monitored for at least twelve weeks following vector administration. During this time, the subject should not demonstrate a serious adverse reaction related to vector administration, and human factor IX circulating in the subject's bloodstream should become detectable at a level of approximately 5% of the level typically observed in normal healthy persons without hemophilia. A second, 3-fold higher dose (approximately $3 \times 10^{12}$ vg/kg) of huAAV2-hFIX can then be administered to the same subject in a manner similar to that used for the first dose. Following administration of the second dose, the huAAV2-hFIX vector should transfer additional copies of the hFIX gene to liver hepatocytes. The subject will then be monitored on an ongoing basis, and it is predicted will exhibit no serious adverse reactions related to vector administration. Several weeks after administration of the second dose of huAAV2-hFIX vector, the level of circulating hFIX in the subjects bloodstream should increase, and stabilize at a concentration corresponding to approximately 20% of the normal level. This hFIX expression can be attributed to gene transfer using huAAV2-hFIX, and should be detectable on an ongoing basis for at least the next three years. The severe hemophila B phenotype should therefore be converted to a mild hemophilia B phenotype, resulting in improved quality of life and reduced exposure to risks typically associated with severe hemophilia B.

Example 5

Figure 13:
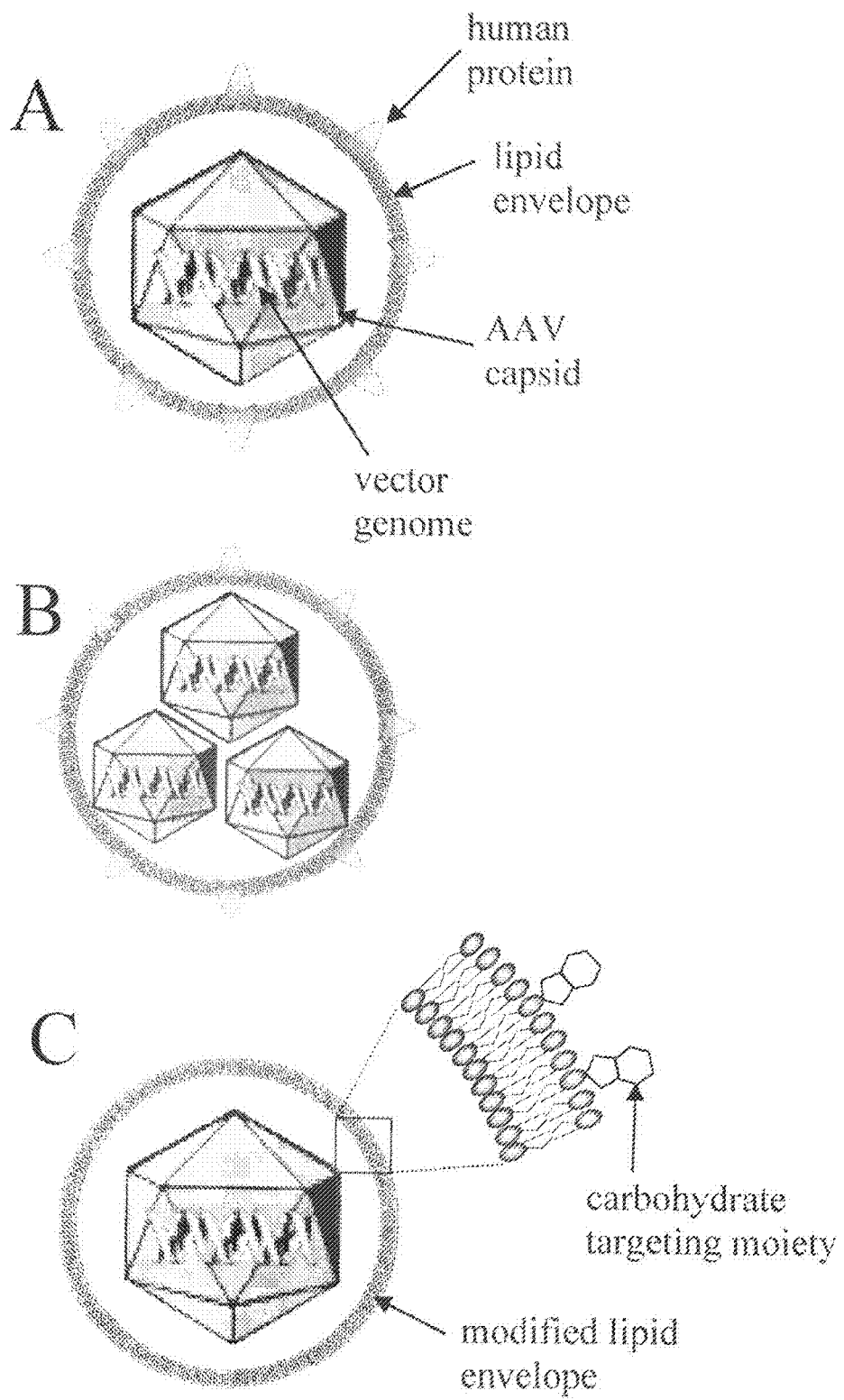
FIG. 13. Schematic representation of lipid-enveloped versions of humanized AAV vectors. The picture in Panel A shows one example of an enveloped huAAV vector, which is composed of: 1) the vector genome (therapeutic expression cassette flanked by AAV inverted terminal repeats); 2) the vector genome is packaged within the AAV capsid; 3) the vector genome-containing AAV capsid is surrounded by a lipid envelope, for example, a unilamellar lipid bilayer; 4) associated with the lipid envelope are human proteins (non immunogenic masking and targeting moieties) that bind specifically to receptors on desired target cells (non immunogenic targeting moieties). The surface of the enveloped humanized AAV vector exposed to human blood, lymph, or other body fluids that may contain antibodies, is composed of components that are predicted to not be recognized by antibodies, whether pre existing or induced as a result of administration of huAAV vectors. The picture in Panel B shows an example of an enveloped huAAV vector in which three AAV capsid particles, each containing a vector genome, are contained within a single lipid envelope. One or more AAV capsid particles may be contained within lipid envelopes. The picture in Panel C shows an example of an enveloped huAAV vector which is surrounded by a modified lipid envelope lacking associated human proteins. This modified enveloped huAAV vector contains lipid constituents with an attached carbohydrate moiety that enables targeting to a desired human cell following in vivo administration. Alternatively, lipid-enveloped versions of humanized AAV vectors can contain both human proteins and lipids with attached carbohydrate moieties to enhance the strength and specificity of target cell binding. The lipid-enveloped versions of humanized AAV vectors described herein preferably comprise all of the described components i.e. 1) the vector genome; 2) the AAV capsid shell; 3) the lipid envelope; and 4) the non immunogenic targeting moieties in combination.
Figure 14:
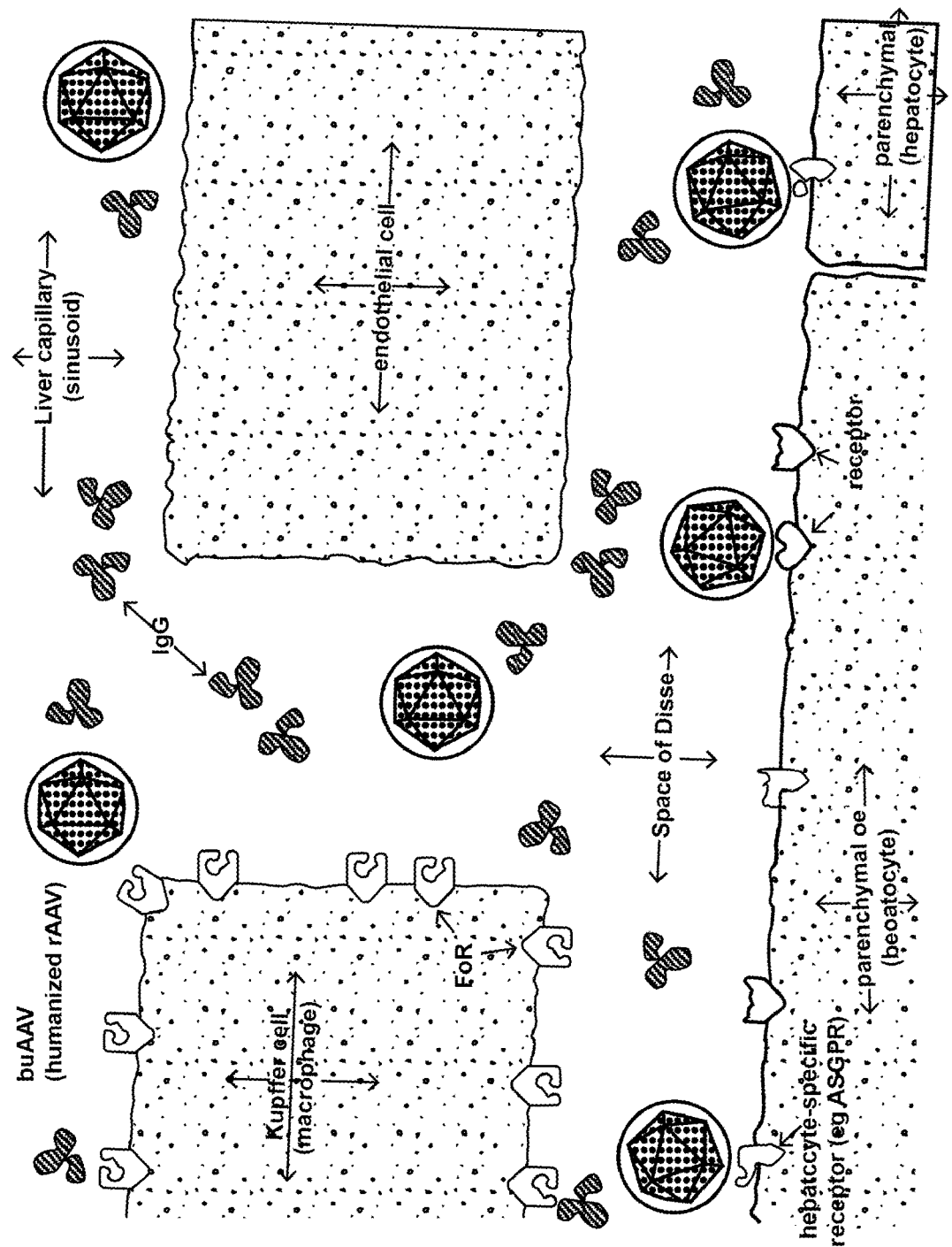
FIG. 14. Pathways and fate of blood-borne lipid-enveloped versions of humanized AAV vectors. Lipid enveloped versions of humanized AAV particles are not opsonized by antibodies, not bound by antigen-presenting cells such Kupffer cells expressing Fc Receptors, and therefore are less likely to activate an immune response. Instead, the lipid-enveloped versions of humanized AAV vectors should bypass the antigen presenting cells, thereby reaching and successfully transducing the intended target cells, in this case hepatocytes. To achieve targeting to hepatocytes, human Apo A-I is one example of a targeting protein that could be used, and phosphoethanolamine-N-lactosyl (Lactosyl PE) is one example of a targeting lipid containing a carbohydrate moiety that could be used to bind to receptors on hepatocytes.

The following prophetic example describes an alternative approach to making humanized AAV vector to treat hemophilia B. AAV2 expressing human coagulation factor IX (hFIX) under the control of a hepatocyte specific promoter (e.g. Manno et al, 2006) is manufactured using methods appropriate to ensure purity and quality as required for clinical (human) administration (e.g. as described in: Wright (2008). Manufacturing and characterizing AAV-based vectors for use in clinical studies. Gene Therapy 15:840-848). In this example, a lipid-enveloped version of humanized AAV2-hFIX is manufactured. Highly purified AAV2-hFIX vector is adjusted to a concentration of approximately $1 \times 10^{13}$ vg/mL in neutral buffered saline solution. The AAV2-hFIX is mixed with 1-palmitoyl-2-oleoyl-sn-glycero-3-phosphocholine (POPC) at a concentration of 100 mg/mL. The appropriate grade (GMP grade) of POPC for use as a raw material for preparation of a clinical grade huAAV vector is obtained from a commercial source such as Avanti Polar Lipids, Inc (Alabaster, Ala.). To this mixture is added highly purified human apolipoprotein A-I at a concentration of approximately 1 mg/mL. The human apolipoprotein A-I (Apo A-I) is prepared using methods and controls appropriate for manufacturing of a component used for the preparation of a human parenteral product. In place of Apo A-I, other human proteins may be used, for example other human apolipoproteins. The mixture is vortexed five times, each time for approximately 30 s, with approximately 10 s between each vortexing. A lipid vesicle extruder such as the apparatus available from Esperion Therapeutics, Inc (Ann Arbor, Mich.) is used to create vesicles according to the manufacturer's instructions. The extruder is fitted with a 0.1 micrometer polycarbonate filter, and vesicles are created using the AAV2-hFIX/POPC/Apo A-I mixture. Under these conditions, vesicles of an approximate diameter of 100 nm are produced. Vesicles containing AAV2-hFIX are concentrated and separated from vesicles lacking AAV2-hFIX by centrifugation. The separation is based on the higher density of vesicles containing AAV-hFIX, which will sediment more rapidly to the bottom of the centrifugation tube. The concentrated lipid-enveloped humanized AAV2-hFIX vectors recovered from the centrifugation tube (see FIG. 13, Panels A and B) are exchanged into a formulation buffer appropriate for human parenteral administration using tangential flow filtration. The product is then subjected to appropriate characterization and quality control testing to ensure its purity, potency and safety, and then administered to human subjects suffering from hemophilia B as described in the previous example.

Example 6

The following prophetic example describes an alternative approach to making humanized AAV vector to treat hemophilia B. AAV2 expressing human coagulation factor IX (hFIX) under the control of a hepatocyte specific promoter (e.g. Manno et al, 2006) is manufactured using methods appropriate to ensure purity and quality as required for clinical (human) administration. In this example, an alternative lipid-enveloped version of humanized AAV2-hFIX is manufactured. Highly purified AAV2-hFIX vector is adjusted to a concentration of approximately $1 \times 10^{13}$ vg/mL in a neutral buffered saline solution. The AAV2-hFIX is mixed with 1-palmitoyl-2-oleoyl-sn-glycero-3-phosphocholine (POPC) at a concentration of 100 mg/mL. The appropriate grade (GMP grade) of POPC for use as a raw material for preparation of a clinical grade huAAV vector is obtained from a commercial source such as Avanti Polar Lipids, Inc. To this mixture is added phosphoethanolamine-N-lactosyl (Lactosyl PE) at a concentration of 20 mg/mL. The appropriate grade (GMP grade) of Lactosyl PE for use as a raw material for preparation of a clinical grade huAAV vector is obtained from a commercial source such as Avanti Polar Lipids, Inc. In place of Lactosyl PE, other lipids or surfactants such as galactosylated pluronic F38, F68 or F108 can be used at a similar concentration. Pluronic F38, F68, or F108 can be obtained from BASF (Germany) and enzymatically galactosylated with substrate p-nitrophenyl β-dD-galactopyranoside (pNP-β-gal) (Sigma-Aldrich) using the enzyme β-galactosidase from *Aspergillus oryzae* (Sigma-Aldrich). The mixture is vortexed five times, each time for approximately 30 s, with approximately 10 s between each vortexing. A lipid vesicle extruder such as the apparatus available from Esperion Therapeutics, Inc (Ann Arbor, Mich.) is used to create vesicles according to the manufacturer's instructions. The extruder is fitted with a 0.1 micrometer polycarbonate filter, and vesicles are created using the AAV2-hFIX/POPC/Lactosyl PE mixture. Under these conditions, vesicles of an approximate diameter of 100 nm are produced. Vesicles containing AAV2-hFIX are concentrated and separated from vesicles lacking AAV2-hFIX by centrifugation. The separation is based on the higher density of vesicles containing AAV-hFIX, which will sediment more rapidly to the bottom of the centrifugation tube. The concentrated lipid-enveloped humanized AAV2-hFIX vectors recovered from the centrifugation tube (see FIG. 13, Panel C) are exchanged into an appropriate formulation buffer for parenteral administration using tangential flow filtration. The product is then subjected to appropriate characterization and quality control testing to ensure its purity, potency and safety, and then administered to human subjects suffering from hemophilia B as described in Example 4.

REFERENCES

Beck J F, et al (2003). Director observation of covalent adducts with Cys34 of human serum albumin using mass spectrometry. Analytical Biochem. 325:326-336.

Cerenzia M T, et al (1996). Adenine arabinoside monophosphate couple to lactosaminated human albumin administered for 4 weeks in patients with chronic type B hepatitis decreases viremia without producing significant side effects. Hepatology 23:657-661.

Fabisiak J P, et al (2002). Quantification of oxidative/nitrosative modification of Cys34 in human serum albumin using a fluorescence-based SDS-PAGE assay. ZZZ Flotte T R (2004). Immune responses to recombinant adeno-associated virus vectors: Putting preclinical findings into perspective. Human Gene Ther. 15:716-717.

Gao G P Alvira M R, Wang L, Calcedo R, Johnston, J. Wilson J M (2002). Novel adeno-associated viruses from rhesus monkeys as vectors for human gene therapy. Proc. Natl. Acad Sci. U.S.A. 99:11854-11859

He X M, and Carter D C. (1992). Atomic structure and chemistry of human serum albumin. Nature (London) 358:209-215.

Herzog R W, et al (1999) Long-term correction of canine hemophilia B by gene transfer of blood coagulation factor IX mediated by adeno-associated viral vectors. Nat. Med 5:56-63.

High K A, et al (2003). Immune responses to AAV and to Factor IX in a Phase I study of AAV-mediated, liver-directed gene transfer for hemophilia B. Blood 102:154a-155a.

Kragh-Hansen U, et al (23001). Detergents as probes of hydrophobic binding cavities in serum albumin and other water soluble proteins. Biophys. J. 8: 2898-2911.

Kurtzhals P, et al (1995). Albumin binding of insulins acylated with fatty acids: Characterization of the ligand-protein interaction and correlation between binding affinity and timing of the insulin effect in vivo. Biochem J. 312:725-731.

Le H T, Yu Q C, Wilson J M, Croyle M A (2005). Utility of PEGylated recombinant adeno-associated viruses for gene transfer. J. Control. Release 108:161-177.

Lewis A D, Chen R, Montefiori D C, Johnson P R, Clark K R (2002). Generation of neutralizing activity against human immunodeficiency virus type 1 in serum by antibody gene transfer. J. Virol 76:8769-8775.

Manno, C. S., Arruda, V. R., Pierce, G. F, Glader, B., Ragni, M., Rasko, J., Ozelo, M. C., Hoots, K., Blatt, P. Konkle, B., Dake, M., Kaye, R., Razavi, M., Zajko, A., Zehnder, J. Nakai, H., Chew, A., Leonard, D., Wright, J. F., Lessard, R. R., Sommer J. M., Tigges, M., Sabatino, D., Luk, A., Jiang, H., Mingozzi, F., Couto, L, Ertl, H. C., High, K. A., Kay, M. A.: Successful transduction of liver in hemophilia by AAV-factor IX and limitations imposed by the host immune response. Nature Medicine 12:342-347, 2006.

Meijer D K F and Molemaq G (1995). Targeting of drugs to the liver. Seminars in Liver Disease 15:202-256.

Peters, Theodore Jr. (1996). All about albumin. Biochemistry, genetics, and medical applications. Academic Press, San Diego.

Flou F J and Ballesteros A (1994). Acylation of subtilisin with long fatty acyl residues affects it activity and thermostability in aqueous medium FEBS Lets 339:200-204.

Reyes-Sandoval, A, Ertl H C J (2003). CpG methylation of a plasmid vector results in extended transgene product expression by circumventing induction of immune responses. Mol. Therapy 9:249-261.

Scallan C D, et al (2003). Sustained phenotypic correction of canine hemophilia A using an adeno-associated virus vector. Blood 102: 2031-2037.

Snyder R O, Miao, C, Meuse L, Tubb J, Donahue B A, Lin H F, Stafford D W, Patel S, Thompson A R, Nichols T, Read M A S, Belleinger D A, Brinkhous K M, Kay M A. (1999). Correction of hemophilia B in canine and murine models using recombinant adeno-associated viral vectors. Nature Medicine 5:64-70.

Wright et al (2005). Identification of factors that contribute to recombinant AAV2 particle aggregation and methods to prevent its occurrence during vector purification and formulation. Mol. Therapy 12:171-178.

Wright, J. F., and Qu, G.: Large-scale recombinant adeno-associated virus (rAAV) production and purification. U.S. Pat. No. 6,593,123.

Xie Q, et al (2002). The atomic structure of adeno-associated virus (AAV-2), a vector for human gene therapy. Proc. Natl. Acad. Sci. U.S.A. 99:10405-10410.

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. A humanized adeno-associated viral vector capable of transducing a target cell, the viral vector comprising:
  a) a capsid surface;
  b) a transgene encoding a therapeutic protein or therapeutic nucleic acid molecule of interest; and
  c) a plurality of human surface molecules attached to the capsid surface, wherein the human surface molecules comprise human serum albumin and the human surface molecules are covalently cross-linked to the capsid surface, such that the plurality of human surface molecules
    (i) reduces or blocks binding of an antibody to the viral vector, or
    (ii) reduces or blocks antibody-mediated clearance of the viral vector, wherein the viral vector exhibits at least 4-fold greater resistance to neutralization by monoclonal antibody A20 compared to a second adeno-associated viral vector comprising the capsid surface and the transgene, but lacking the plurality of human surface molecules.

2. The viral vector of claim 1, wherein the viral vector comprises an average particle radius in a range of 16.6 nm to 18.3 nm as determined by a dynamic light scattering assay.

3. The viral vector of claim 1, wherein the therapeutic protein is selected from the group consisting of a cystic fibrosis transmembrane regulator protein, dystrophin, utrophin, Factor XIII, Factor IX, Factor X, a monoclonal antibody, erythropoietin, an LDL receptor, lipoprotein lipase, ornithine transcarbamylase, β-globin, α-globin, spectrin, α-antitrypsin, a human apolipoprotein, adenosine deaminase, hypoxanthine guanine phosphoribosyl transferase, β-glucocerebrosidase, sphingomyelinase, lysosomal hexosaminidase, branched-chain keto acid dehydrogenase, a hormone, insulin-like growth factor 1, insulin-like growth factor 2, platelet derived growth factor, epidermal growth factor, nerve growth factor, neurotrophic factor-3, neurotrophic factor-4, brain-derived neurotrophic factor, glial derived growth factor, transforming growth factor α, transforming growth factor β, a cytokine, α-interferon, β-interferon, interferon-γ, interleukin-2, interleukin-4, interleukin-12, granulocyte-macrophage colony stimulating factor, lymphotoxin, a suicide gene product, herpes simplex virus thymidine kinase, cytosine deaminase, diphtheria toxin, cytochrome P450, deoxycytidine kinase, tumor necrosis factor, a tumor suppressor gene product, p53, Rb, Wt-1, NF1, VHL and APC.

4. The viral vector of claim 3, wherein the therapeutic protein is human Factor IX.

5. A pharmaceutical preparation comprising the viral vector of claim 1 and a pharmaceutically acceptable carrier.

6. The humanized adeno-associated viral vector of claim 1, wherein the transgene encodes a therapeutic clotting factor.

7. The viral vector of claim 1 or 2, wherein the resistance to neutralization is determined by a virus transduction assay using HepG2 cells and a fixed concentration of viral particles in an amount of $1\times10^{11}$ vg/mL.

8. The viral vector of claim 1 or 2, wherein the viral vector exhibits up to 68-fold greater resistance to neutralization by monoclonal antibody A20 compared to the second adeno-associated viral vector when a measured transduction amount of the viral vector and the second adeno-associated viral vector is normalized to transducing units.

9. The viral vector of claim 8, wherein the resistance to neutralization after normalizing is in a range of 16-fold to 68-fold greater.

10. A method for delivering a transgene to a cell comprising administration of an effective amount of the humanized adeno-associated viral vector of claim 1 to a patient in need thereof.

11. The method of claim 10, wherein said patient has a clotting disorder and said transgene encodes a clotting factor.

12. The method of claim 11, wherein said clotting factor is hFIX.

* * * * *